(12) United States Patent
Jang et al.

(10) Patent No.: US 10,274,824 B2
(45) Date of Patent: Apr. 30, 2019

(54) PHOTOBASE GENERATORS AND PHOTORESIST COMPOSITIONS COMPRISING SAME

(71) Applicant: Rohm and Haas Electronic Materials Korea Ltd., Cheonan, Chungcheongnam-Do (KR)

(72) Inventors: Min-Kyung Jang, Seoul (KR); Eui Hyun Ryu, Gyeonggi-do (KR); Chang-Young Hong, Chungbuk (KR); Myung Yeol Kim, Gyeonggi-do (KR); Jung-June Lee, Ghungcheongnam-do (KR); Dong Je Hong, Gyeonggi-do (KR); Dong-Yong Kim, Gyeonggi-do (KR); Hae-Jin Lim, Yonsu-Gu (KR); Jae Yun Ahn, Busan (KR); Ohk-Min Jeon, Chungcheongnam-do (KR)

(73) Assignee: Rohm and Haas Electronic Materials Korea Ltd., Cheonan, Chungcheongnam-do (KR)

( * ) Notice: Subject to any disclaimer, the term of this patent is extended or adjusted under 35 U.S.C. 154(b) by 0 days.

(21) Appl. No.: 15/153,310

(22) Filed: May 12, 2016

(65) Prior Publication Data

US 2016/0334703 A1 Nov. 17, 2016

Related U.S. Application Data

(60) Provisional application No. 62/162,584, filed on May 15, 2015.

(51) Int. Cl.
| | | |
|---|---|---|
| G03F 7/20 | (2006.01) |
| G03F 7/32 | (2006.01) |
| G03F 7/004 | (2006.01) |
| G03F 7/039 | (2006.01) |
| C07C 271/12 | (2006.01) |
| C07C 271/14 | (2006.01) |

(52) U.S. Cl.
CPC .......... *G03F 7/0045* (2013.01); *C07C 271/12* (2013.01); *C07C 271/14* (2013.01); *G03F 7/0046* (2013.01); *G03F 7/0397* (2013.01); *G03F 7/2041* (2013.01); *G03F 7/322* (2013.01); *G03F 7/325* (2013.01); *C07C 2603/14* (2017.05)

(58) Field of Classification Search
None
See application file for complete search history.

(56) References Cited

U.S. PATENT DOCUMENTS

| | | | |
|---|---|---|---|
| 6,790,579 B1 | 9/2004 | Goodall et al. | |
| 9,488,911 B2 * | 11/2016 | Tsuchimura | C07D 277/64 |
| 2006/0172149 A1 | 8/2006 | Ahn et al. | |
| 2007/0190451 A1 | 8/2007 | Ishii et al. | |
| 2011/0233048 A1 * | 9/2011 | Kuramoto | C07C 271/12 204/157.82 |
| 2012/0058428 A1 * | 3/2012 | Hatakeyama | G03F 7/0035 430/283.1 |
| 2013/0177853 A1 | 7/2013 | Shimizu et al. | |
| 2013/0344436 A1 | 12/2013 | Nakamura et al. | |
| 2014/0038102 A1 | 2/2014 | Park et al. | |
| 2014/0356785 A1 * | 12/2014 | Williams, III | G03F 7/0045 430/270.1 |
| 2015/0362836 A1 * | 12/2015 | Tsuchimura | C07D 277/64 430/270.1 |

FOREIGN PATENT DOCUMENTS

| | | | |
|---|---|---|---|
| EP | 1702962 A1 | 9/2006 | |
| JP | H10-077257 A | 3/1998 | |
| JP | H11337722 A | 12/1999 | |
| JP | 2010-133996 | * | 6/2010 |
| JP | 2010-133996 A | 6/2010 | |
| JP | 2012-180310 | * | 9/2012 |
| JP | 2014-163999 A | 9/2014 | |
| KR | 20110106859 A | 9/2011 | |
| TW | 201029961 A | 8/2010 | |
| TW | 201439062 A | 10/2014 | |
| WO | WO 2014/129250 A1 * | 8/2014 | |

OTHER PUBLICATIONS

Machine-assisted English translation for JP10-077257 (Yagihashi et al.) (Year: 1998).*
JPO English abstract for JP 2010-133996 (Fukuda et al.) (Year: 2010).*
JPO English abstract for JP2012-180310. (Year: 2012).*
Derwent English abstract for JP10-77257. (Year: 1998).*
English language summary of Office Action dated Jan. 25, 2018 in counterpart Korean Application 10-2016-0054286.
English language summary Office Action dated Nov. 14, 2017 issued in counterpart Taiwan Application 106-2(6)01190-10621156640.
English language summary of KR Office Action dated Aug. 7, 2018 issued in counterpart Korean Application 10-2016-0085331.
English language summary of JP Office Action dated Mar. 23, 2018 issued in counterpart Japanese Application 2016-088986.

* cited by examiner

*Primary Examiner* — Sin J Lee
(74) *Attorney, Agent, or Firm* — Mintz Levin Cohn Ferris Glovsky and Popeo, P.C.; Peter F. Corless

(57) ABSTRACT

New photobase generators suitable for use in photoresists are provided that correspond to Formula (I):

$$X_1-R_1-O-C(=O)N(R_2)R_3 \qquad (I)$$

wherein $X_1$ is an optionally substituted aromatic group; $R_1$ is a linker; and $R_2$ and $R_3$ are the same or different optionally substituted linear, branched or cyclic aliphatic group or an optionally substituted aromatic group, wherein at least one of $R_2$ and $R_3$ is an optionally substituted branched alkyl group having 4 or more carbon atoms.

14 Claims, No Drawings

PHOTOBASE GENERATORS AND PHOTORESIST COMPOSITIONS COMPRISING SAME

CROSS REFERENCE TO RELATED APPLICATION

This application claims the benefit of U.S. Provisional Application No. 62/162,584, filed May 15, 2015, the disclosure of which is hereby incorporated by reference herein in its entirety.

BACKGROUND

The invention relates photobase generators for use in photoresist compositions. The photobase generators comprise one or more branched alkyl groups that can provide enhanced surface activity.

Photoresists are photosensitive films used for the transfer of images to a substrate. A coating layer of a photoresist is formed on a substrate and the photoresist layer is then exposed through a photomask to a source of activating radiation. Following exposure, the photoresist is developed to provide a relief image that permits selective processing of a substrate.

Considerable effort has been made to extend the practical resolution capabilities of positive tone resist development, including in immersion lithography. One such example involves negative tone development (NTD) of a traditionally positive-type chemically amplified photoresist through use of particular developers, typically organic developers such as ketones, esters or ethers, leaving behind a pattern created by the insoluble exposed regions. See, for instance, U.S. Pat. No. 6,790,579.

Certain problems however can result with use of NTD processes. For instance, the relative UV intensity through a resist coating layer is decreased from upper to lower layer regions and from iso contant holes (C/Hs) to dense contact holes (C/Hs). In turn, the concentration of photo-generated acid also varies through a resist layer (acid will be present in decreased amounts in lower resist layer regions) and will vary from iso C/Hs to dense C/Hs. As a result, pattern profiles will exhibit undesirable T-top shapes, pattern collapse and missing contact holes may occur, and iso-dense bias and depth of focus margins may be at unacceptable levels.

Certain basic additives have been employed to attempt to improve resist resolution. See JPH11337722A; US2007190451; EP1702962B1; US20060172149; US20130177853; US20130344436; and US20140038102.

Electronic device manufacturers continually seek increased resolution of a patterned photoresist image. It would be desirable to have new photoresist compositions that could provide enhanced imaging capabilities.

SUMMARY

We now provide new photobase generators that are useful as a photoresist components, including resists used in negative-tone development processes. Preferred photobase generators include at least one carbamate moiety.

More particularly, preferred photobase generators correspond to the following Formula (I):

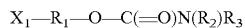

(I)

wherein:
$X_1$ is an optionally substituted aromatic group;
$R_1$ is a linker; and
$R_2$ and $R_3$ are the same or different optionally substituted linear, branched or cyclic aliphatic group or an optionally substituted aromatic group,
wherein at least one of $R_2$ and $R_3$ is an optionally substituted branched alkyl group having 4 or more carbon atoms.

The photobase generator can react upon exposure to activating radiation, such as 193 nm radiation. Upon incorporation into a photoresist composition, the photobase generator can react during lithographic processing of a coating layer of the photoresist composition.

In particular, in preferred systems, the photobase generator can undergo a cleavage reaction upon treatment with radiation for patterning a coating layer of a photoresist composition containing the photobase generator, for example where an amine cleavage product of the photobase generator is produced in the photoresist layer. In certain preferred systems, a secondary amine cleavage product will be produced upon treatment of the photoresist layer with exposure radiation, e.g. 193 nm radiation.

The photobase generator may comprise a variety of aromatic moieties. In certain systems, an aromatic moiety that comprises extended conjugation may be preferred, such as an anthracenyl group or a nitrophenyl. Preferred photobase generators include those of the above Formula (I) where $R_1$ is optionally substituted —$CH_2$— so that $X_1$—$R_1$— is for example optionally substituted nitrobenzyl, anthracenyl methylene. Preferred photobase generators include those of the above Formula (I) where $R_1$ is optionally substituted vinyl i.e. —CH═CH—$CH_2$— so that $X_1$—$R_1$— is optionally substituted styryl and optionally substituted anthracenyl vinyl.

$R_2$ and $R_3$ of Formula (I) (as well as $R_2$ and $R_3$ of Formulae (IA) and (IB) below) each suitably may comprise 4, 5, 6, 7, 8, 9, 10, 11, 12 or more carbon atoms. In certain preferred aspects, $R_2$ and/or $R_3$ may be fluorinated alkyl containing 4, 5, 6, 7, 8, 9, 10, 11, 12 or more carbon atoms. $R_2$ and/or $R_3$ have one or more carbon branches along an alkyl chain, i.e. a carbon in an alkyl chain is further substituted by one or two additional carbon atoms. Preferably, a branched carbon (i.e. a carbon substituted by at least three other carbons) of $R_2$ and/or $R_3$ is proximate to the depicted nitrogen of Formulae (I) (or the depicted nitrogen of Formulae (IA) or (IB) below), for example a branched carbon is separated from the depicted nitrogen by 0, 1, 2 or 3 other non-branched carbons.

Photoresist compositions are also provided that comprise a photobase generator as disclosed herein. In general a photoresist composition suitably comprises: (a) a resin; (b) one or more acid generators; and (c) a photobase generator as disclosed herein.

Photoresists of the invention may be either positive-acting or negative-acting, and preferably are positive-acting.

In a preferred aspect, photoresists of the invention used for short-wavelength imaging applications, such as 193 nm as well as EUV or e-beam imaging.

Particularly preferred photoresists of the invention may be used in immersion lithography applications.

Methods are also provided for forming relief images of photoresist compositions of the invention (including patterned lines with sub-50 nm or sub-20 nm dimensions). Substrates such as a microelectronic wafer also are provided having coated thereon a photoresist composition of the invention.

We have found that use of a present photobase generator compound in a photoresist composition can significantly enhance resolution of a relief image (for example, fine lines) of the resist. In particular, we have found that a photobase generator compound as disclosed herein imparts significantly enhanced lithographic results, including relative to a comparable photoresist that is otherwise identical to the photoresist that instead contains a different basic additive.

DETAILED DESCRIPTION

Photobase Generator Compounds

Preferred photobase generator can have a comparatively reduced surface tension. Without being bond by any theory, such favorable surface activity can provide notable performance benefits, including better photoresist top profiles in a negative tone development process.

As stated above, photobase generators correspond one of the following Formula (I):

wherein:

$X_1$ is an optionally substituted aromatic group;

$R_1$ is a linker; and $R_2$ and $R_3$ are the same or different optionally substituted linear, branched or cyclic aliphatic group or an optionally substituted aromatic group, wherein at least one of $R_2$ and $R_3$ is an optionally substituted branched alkyl group having 4 or more carbon atoms.

In Formulae (I) above (as well as Formulae (IA) and (IB) below), $X_1$ is suitably optionally substituted carbocyclic aryl such as optionally substituted phenyl, naphthyl or anthracenyl or optionally substituted heteroaromatic (one or more ring members of the aromatic ring being N, O or S).

In Formula (I) above (as well as Formulae (IA) and (IB) below), suitable $R_2$ and $R_3$ moieties include those independently chosen from optionally substituted $(C_3-C_{30})$alkyl, optionally substituted $(C_3-C_{30})$heteroalkyl such as $(C_3-C_{30})$alkoxy, $(C_3-C_{30})$alkylsulfide, $(C_3-C_{30})$alkylsulfinyl or $(C_3-C_{30})$alkylsulfonyl).

In Formula (I) above, $R_1$ is a linker which may be a chemical bond or more preferably an optionally substituted alkylene such as $-(CYZ)_n-$ where each Y and Z each is independently hydrogen or a non-hydrogen substituent such as halogen including fluoro, optionally substituted alkyl, optionally substituted alkoxy and the like, and n is a positive integer preferably 1 to 12, with 1 or 2, especially 1 being particularly preferred.

Also preferred is where $R_1$ is an unsaturated group, particularly an alkenylene having 1, 2, 3 or more carbon-carbon double bonds such as $-(CY'=CZ')_n-(CY'Z')_{n'}-$ where each Y' and each Z' is independently hydrogen or a non-hydrogen substituent such as halogen including fluoro, optionally substituted alkyl, optionally substituted alkoxy and the like, and n and n' are each the same or different positive integer preferably 1 to 12. Particularly preferred values for each of n and n' is 1 or 2, especially 1.

Thus, preferred photobase generators include those of the following Formulae (IA) and (IB):

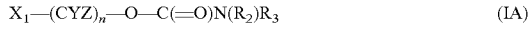

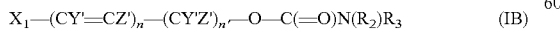

wherein in each of Formulae (IA) and (IB):

$X_1$ is an optionally substituted aromatic group;

each Y, Z, Y', and Z' is independently hydrogen or a non-hydrogen substituent such as halogen including fluoro, optionally substituted alkyl, optionally substituted alkoxy and the like;

n and n' are each positive integer suitably from 1 to 12 an preferably 1 or 2, particularly 1; and $R_2$ and $R_3$ are the same or different optionally substituted linear, branched or cyclic aliphatic group or an optionally substituted aromatic group, wherein at least one of $R_2$ and $R_3$ is an optionally substituted branched alkyl group having 4 or more carbon atoms.

As stated, moieties of Formulae (I), (IA) and (IB) are optionally substituted. Substituted moieties are suitably substituted at one or more available positions by e.g. carboxyl $(-CO_2H)$; carboxy$(C_1-C_{30})$alkyl; $(C_1-C_{30})$alkyl; $(C_1-C_{30})$alkoxy; sulfonyl; sulfonic acid; sulfonate ester; cyano; halo; keto, carbocyclic aryl such as phenyl, napthyl or anthracenyl; heteroaromatic such as $C_{5-30}$ heteroaromtic containing 1-3 N, O or S ring atoms; carboalicyclic (all ring members of the non-aromatic ring being carbon); and optionally substituted heteroalicyclic (one or more ring members of the non-aromatic ring being N, O or S). Preferred substituent groups are carboxyl, carboxy$(C_1-C_{10})$alkyl, $(C_1-C_{10})$alkoxy, sulfonyl, sulfonic acid, sulfonate ester, cyano, halo, and keto; and more preferably carboxyl, carboxy$(C_1-C_8)$alkyl, $(C_1-C_8)$alkoxy, sulfonyl, sulfonic acid, sulfonate ester, cyano, halo, and keto. Preferred ester groups (carboxyalkyl) are carboxy$(C_1-C_6)$alkyl. Preferred alkoxy groups are $(C_1-C_6)$alkoxy, and more preferably $(C_1-C_5)$alkoxy. By "substituted," it is meant that one or more hydrogens on e.g. a carbon atom of the photobase generator compound is replaced with one or more of the above substituent groups. A mixture of such substituent groups may be used. The presence of such substituent groups may impart desired solubility to the photobase generator compound, or may be used to tailor the quenching ability of the photobase generator compound.

Photobase generator compounds useful in the present invention can be readily synthesized. For instance, a substituted amine and a hydroxyl-aromatic compound coupled in the presence of a suitable reagents such as bis-carbonylating reagents such as triphosgene, phosgene.

More particular, as exemplified in the following Scheme A, a secondary amine and substituted anthracene methanol can be coupled with bis-carbonylating reagents such as triphosgene, phosgene under mild conditions.

Scheme A

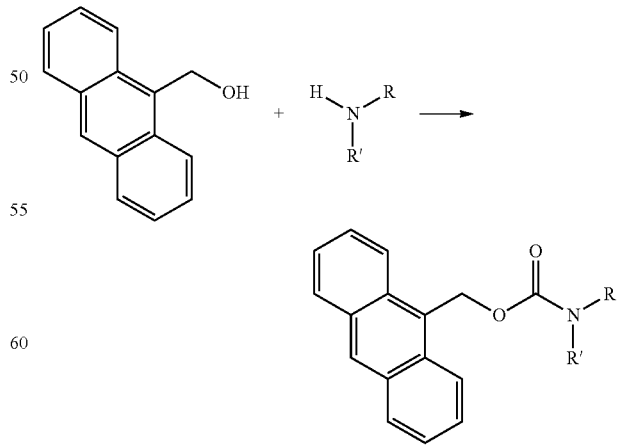

Similarly, as shown in the following Scheme B, a secondary amine and substituted benzyl alcohol can be coupled in the presence of with bis-carbonylating reagents such as triphosgene, phosgene under mild conditions.
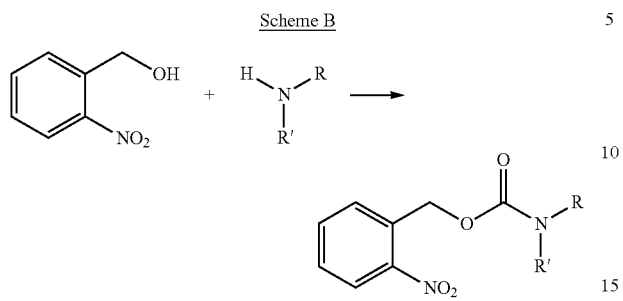
Specifically preferred photobase generator compounds of the invention include the following:
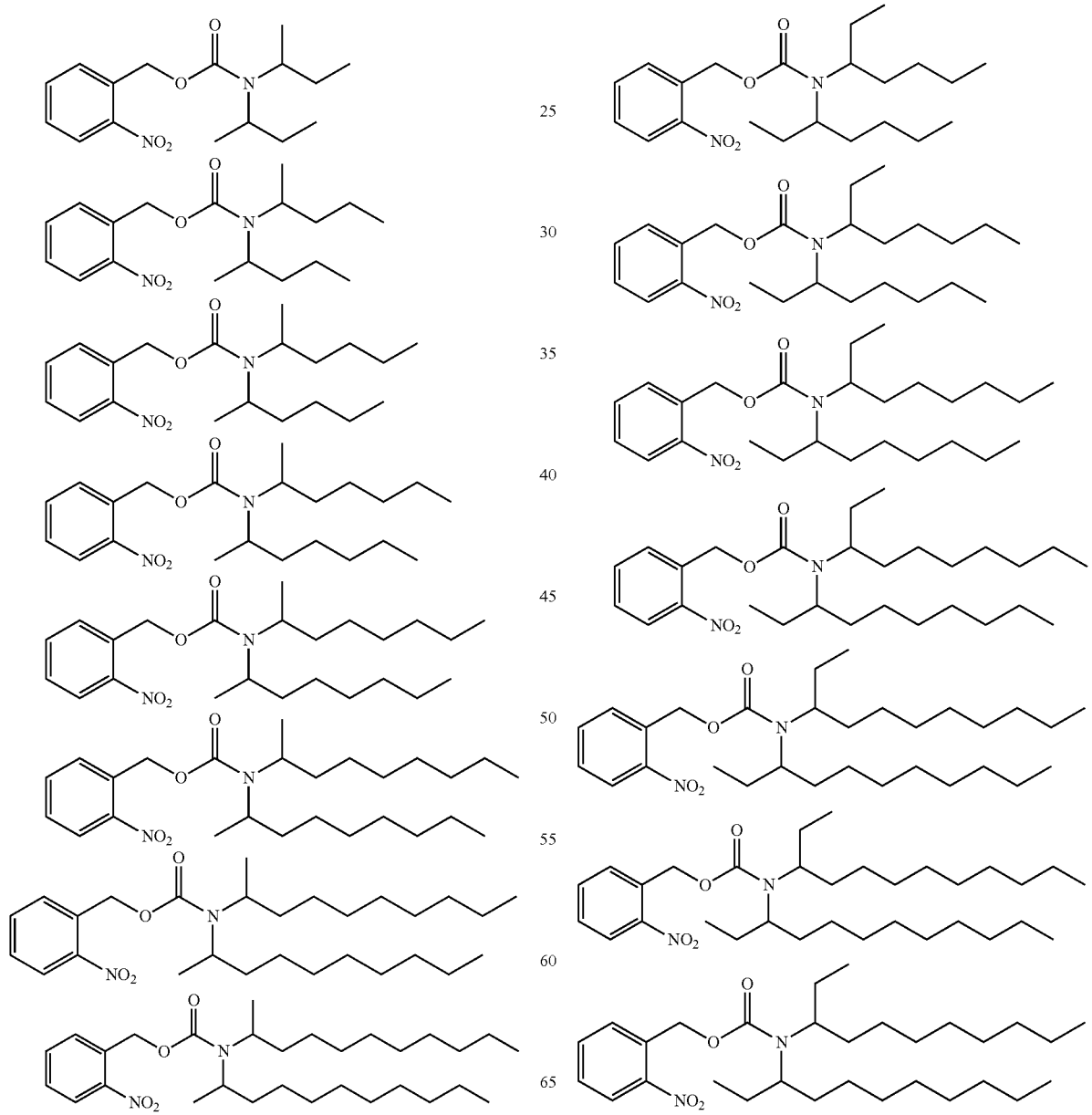

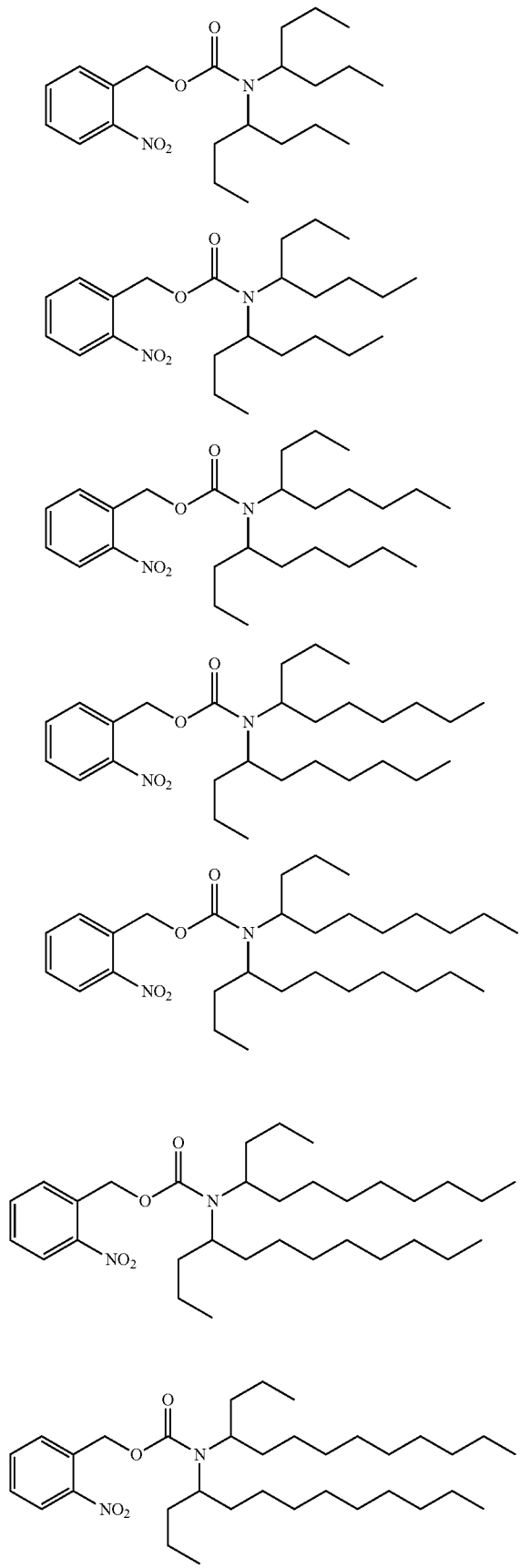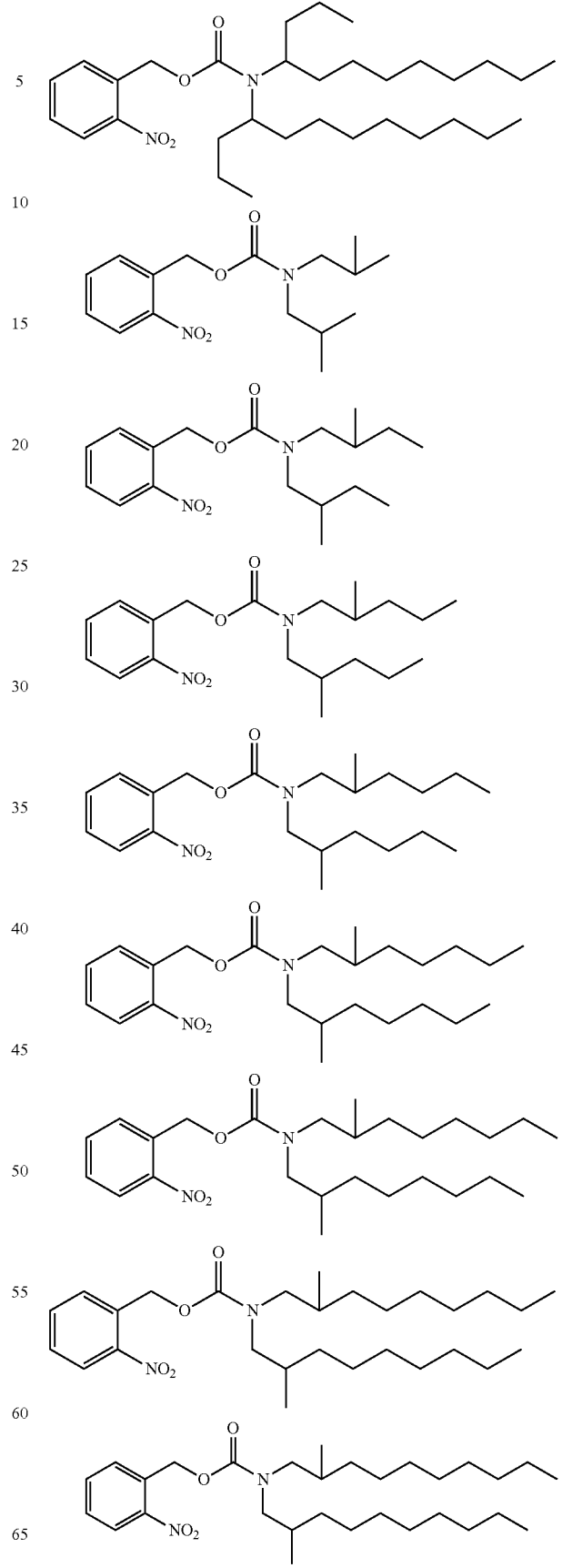

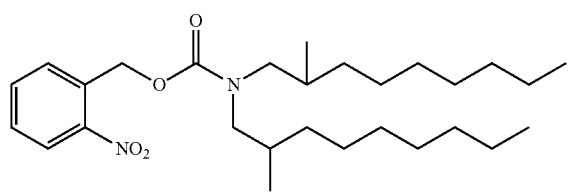
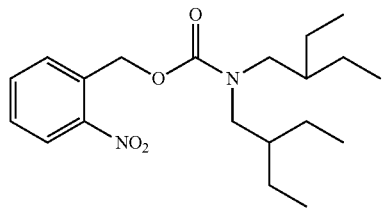
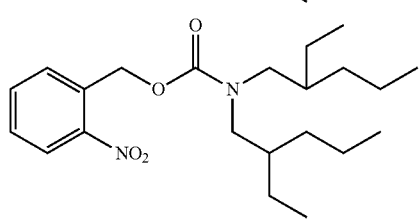
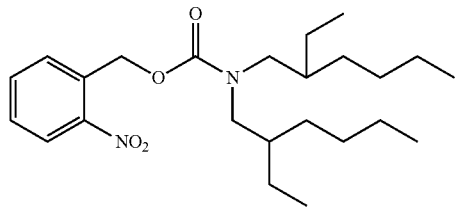
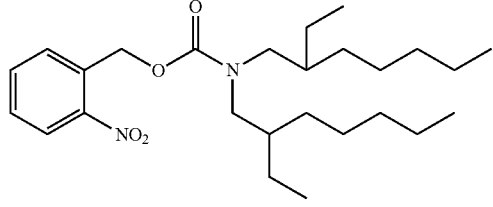
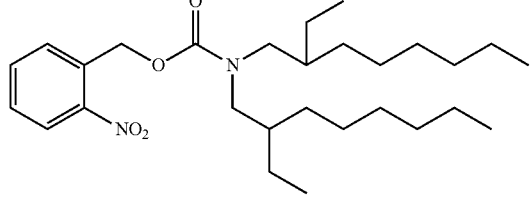
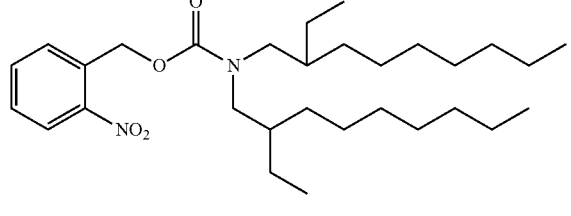
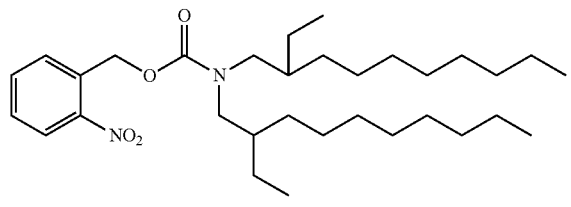
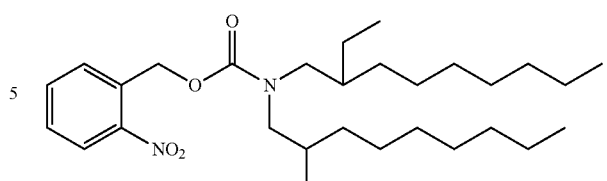
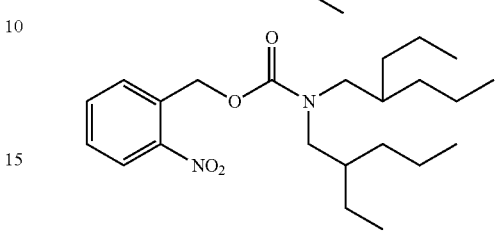
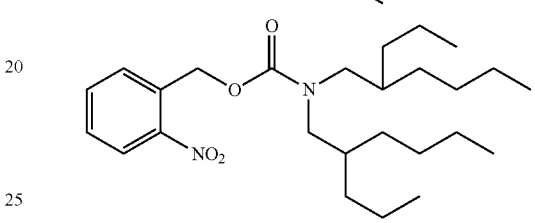
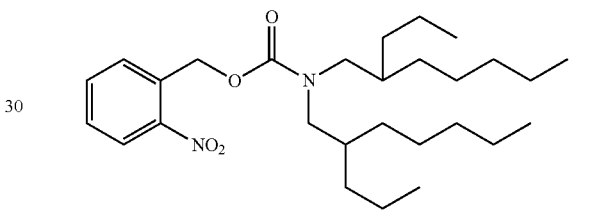
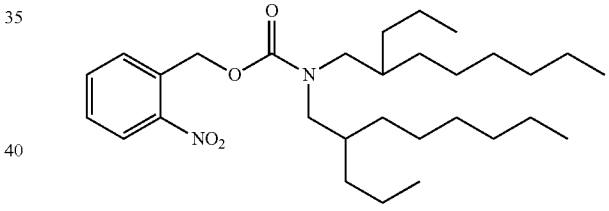
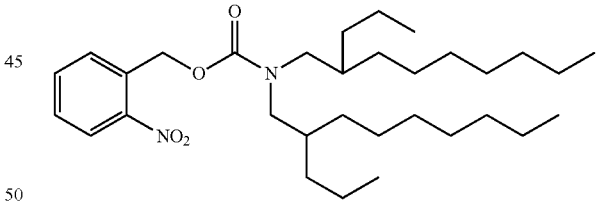
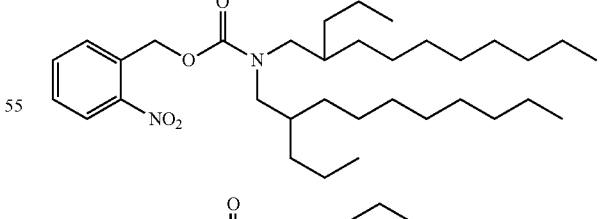
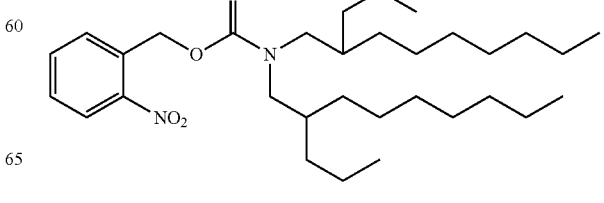

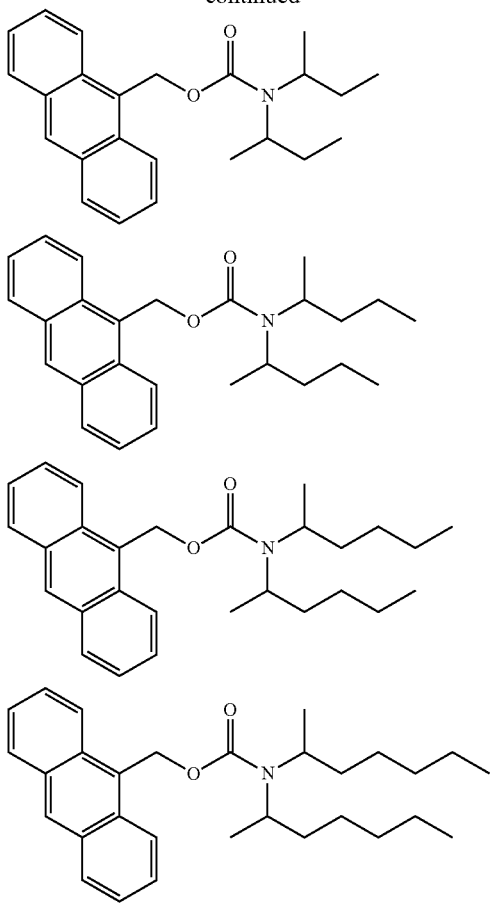
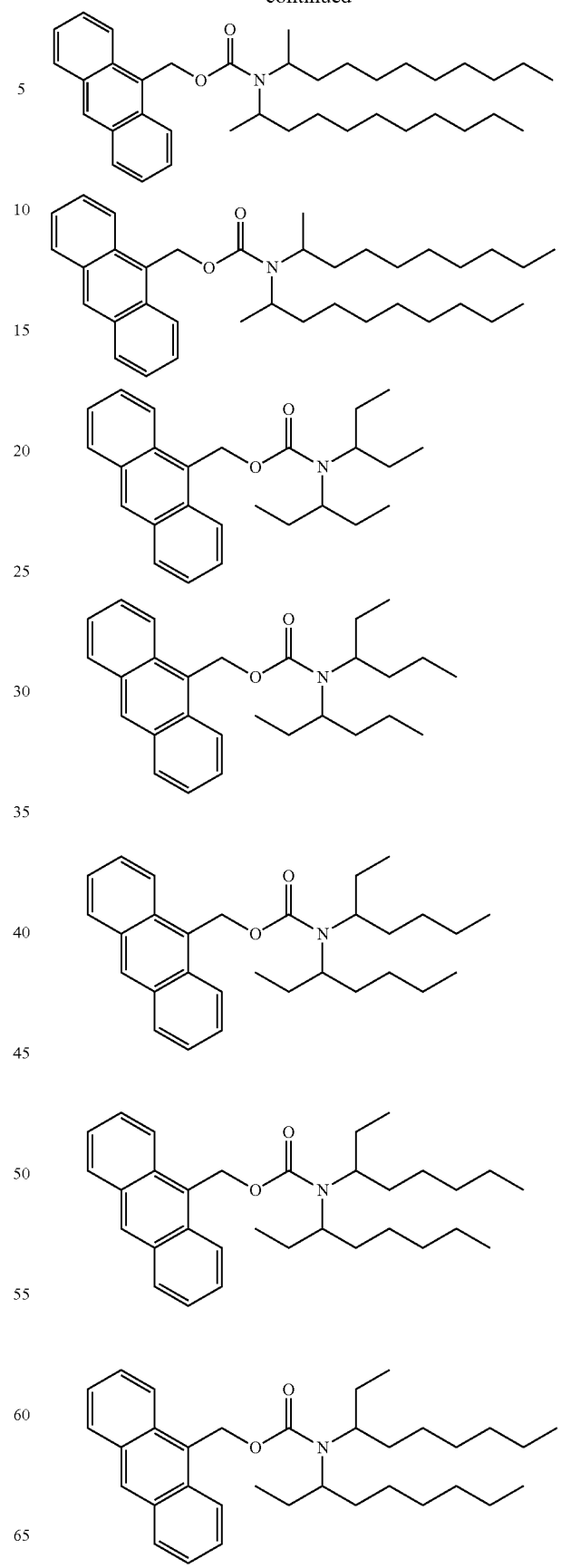

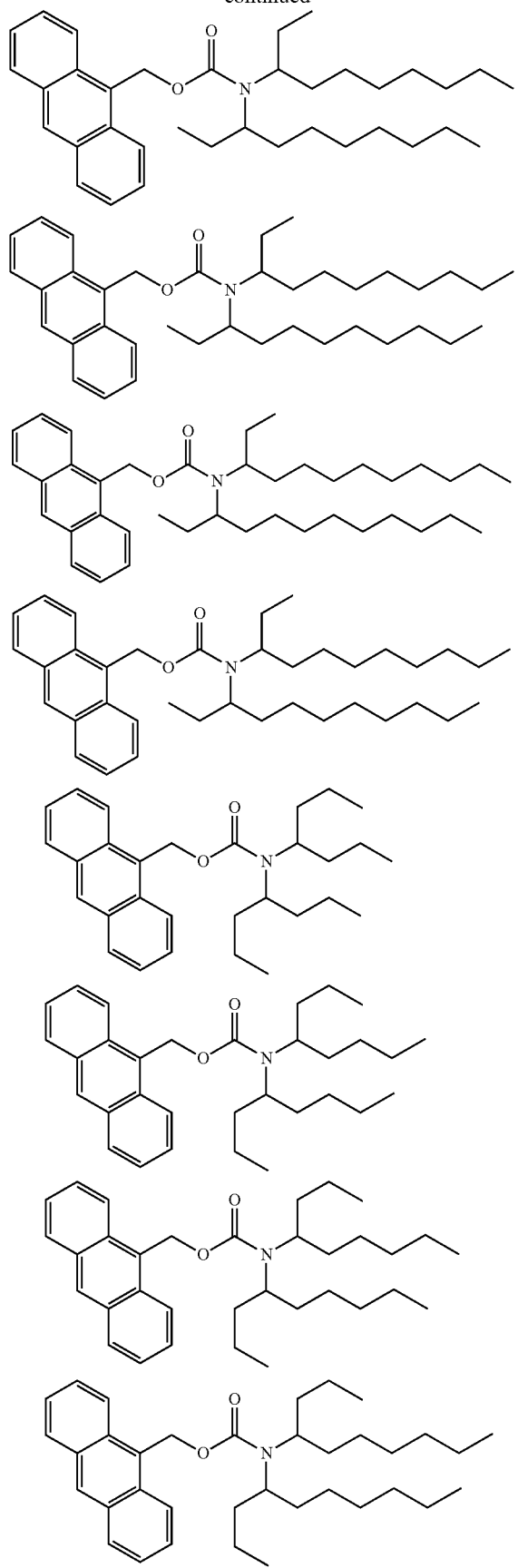
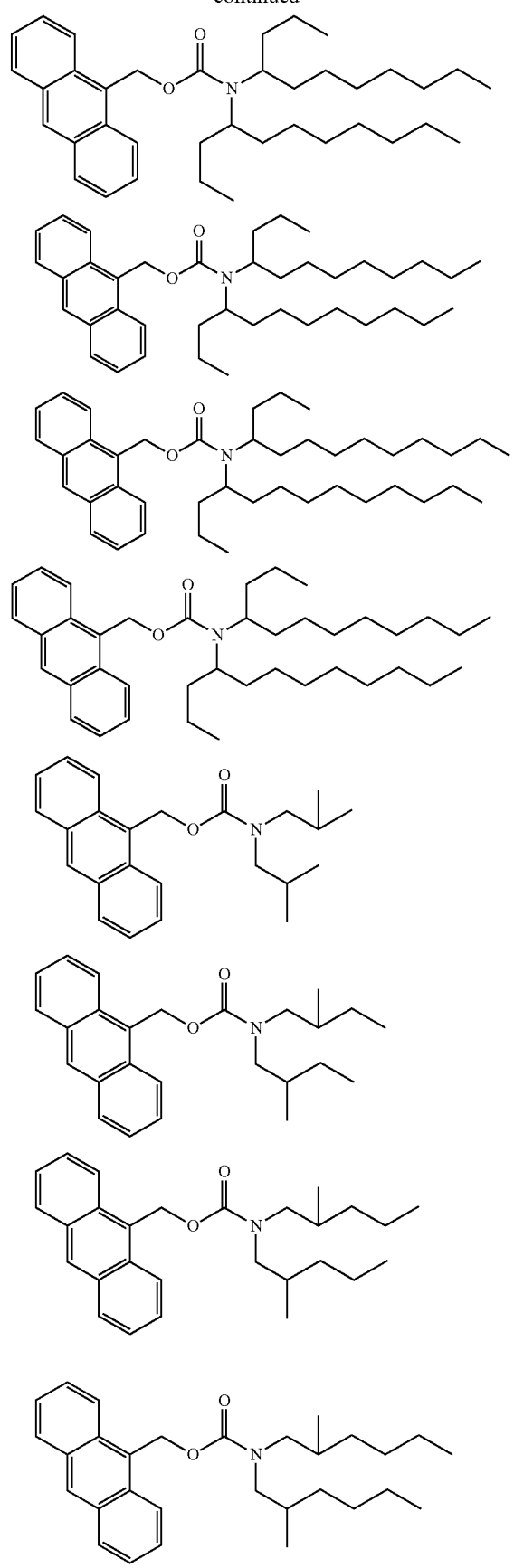

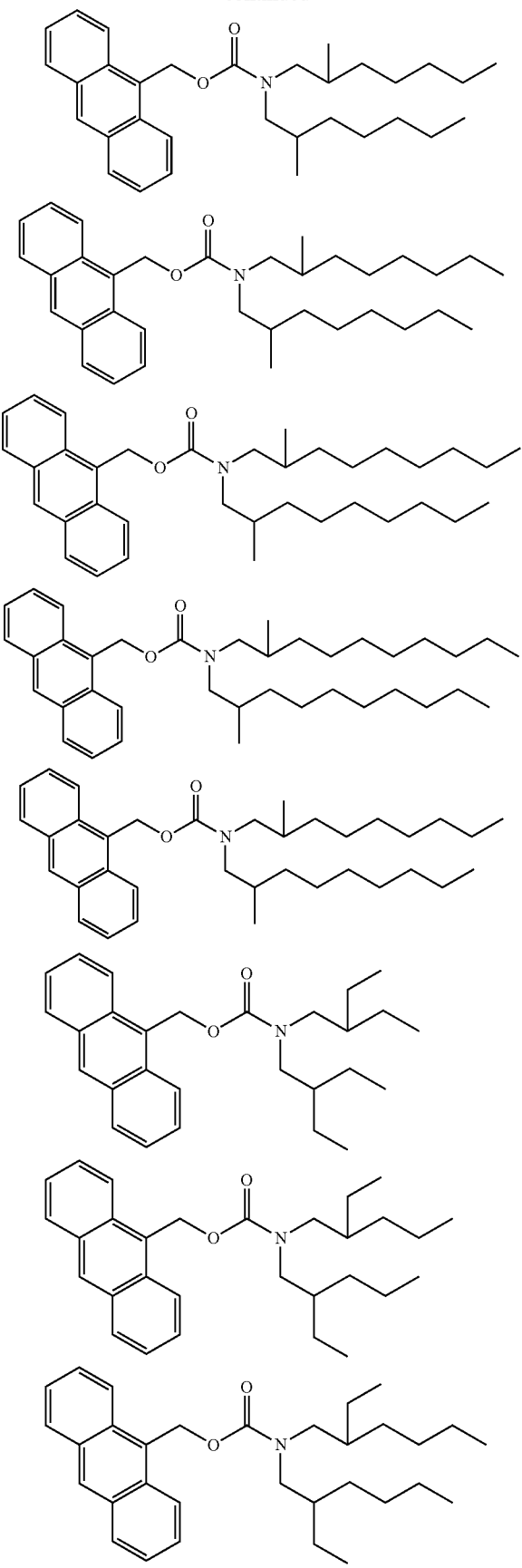
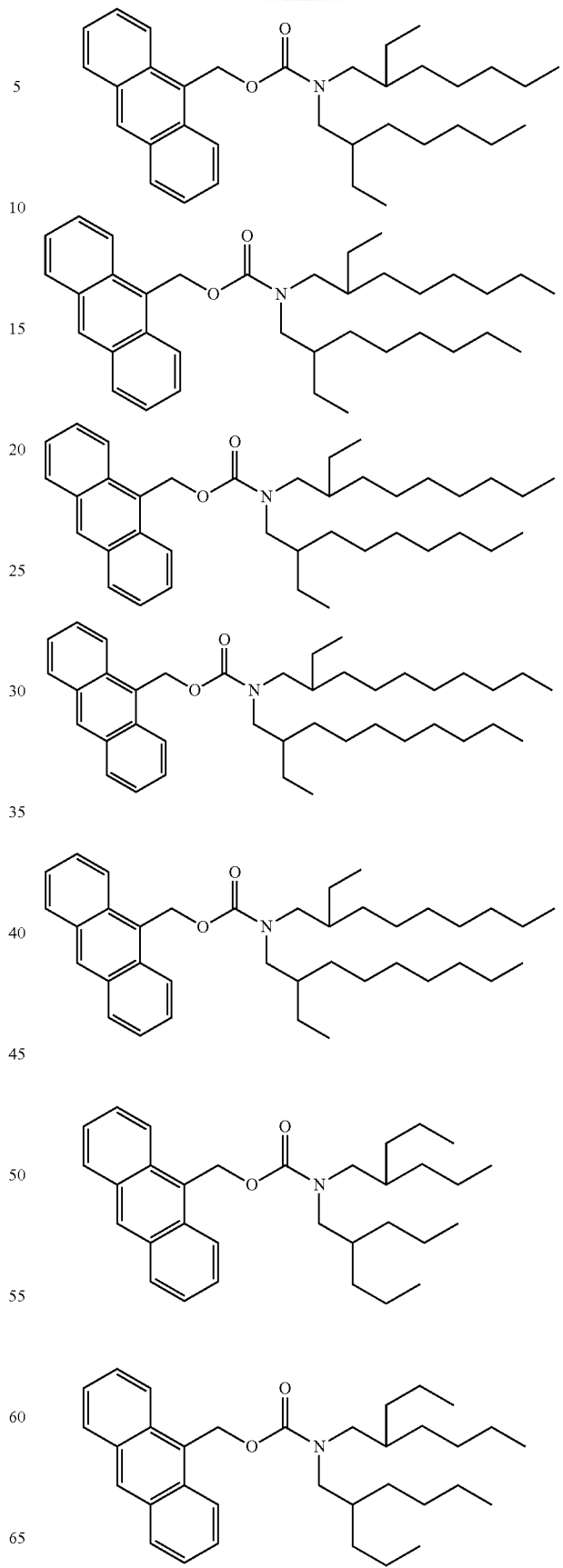

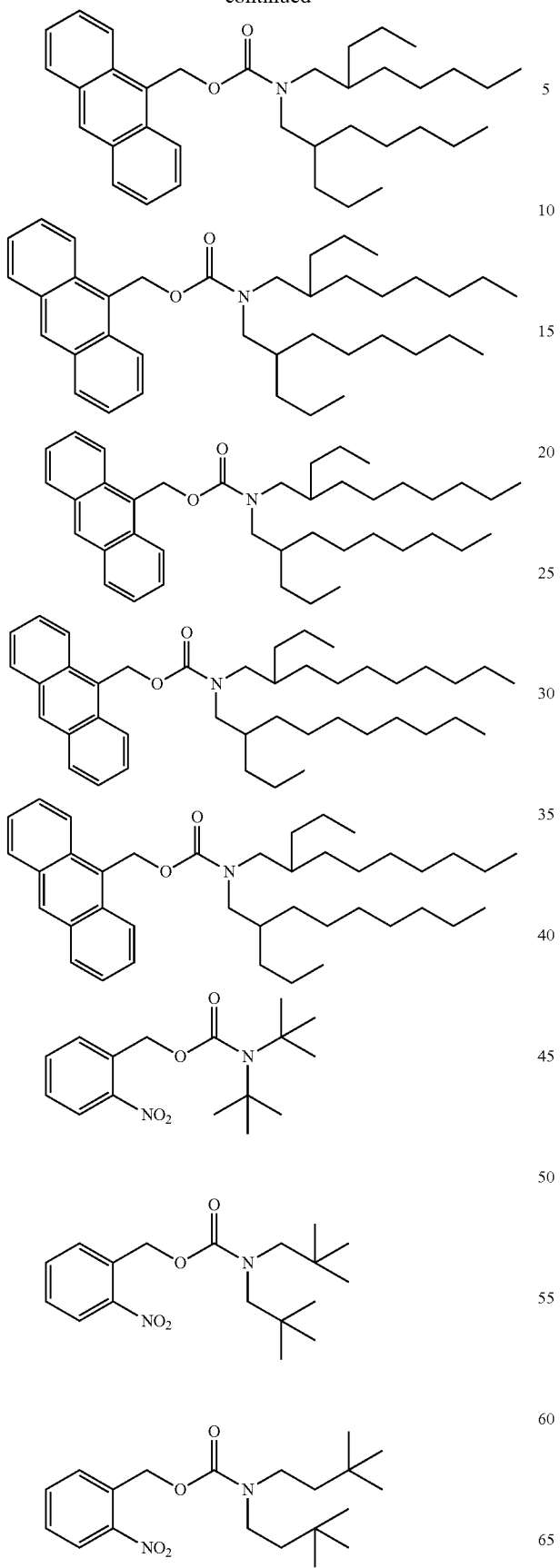

-continued

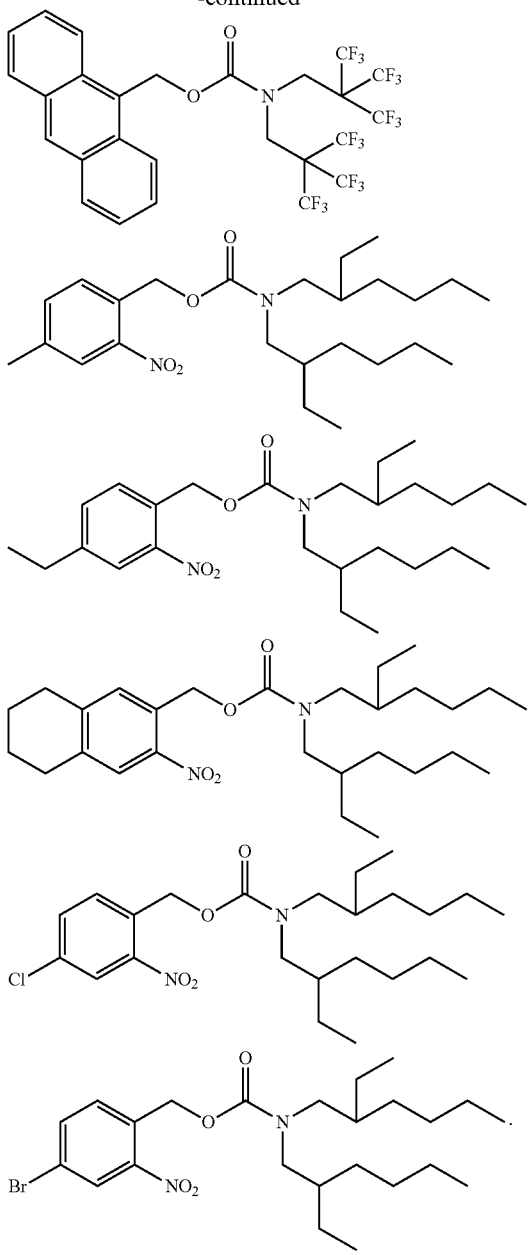

Photoresist Compositions

Photoresists of the invention typically comprise a polymer, one or more acid generators and one or more photobase generator compounds as disclosed herein. Preferably the resist polymer has functional groups that impart alkaline aqueous solubility to the resist composition. For example, preferred are polymers that comprise polar functional groups such as hydroxyl or carboxylate, or acid-labile groups that can liberate such polar moieties upon lithographic processing. Preferably the polymer is used in a resist composition in an amount sufficient to render the resist developable with an aqueous alkaline solution.

Acid generators are also suitably used with polymers that comprise repeat units containing aromatic groups, such as optionally substituted phenyl including phenol, optionally substituted naphthyl, and optionally substituted anthracene. Optionally substituted phenyl (including phenol) containing polymers are particularly suitable for many resist systems, including those imaged with EUV and e-beam radiation. For positive-acting resists, the polymer also preferably contains one or more repeat units that comprise acid-labile groups. For example, in the case of polymers containing optionally substituted phenyl or other aromatic groups, a polymer may comprise repeat units that contain one or more acid-labile moieties such as a polymer that is formed by polymerization of monomers of an acrylate or methacrylate compound with acid-labile ester (e.g. t-butyl acrylate or t-butyl methacrylate). Such monomers may be copolymerized with one or more other monomers that comprise aromatic group(s) such as optionally phenyl, e.g. a styrene or vinyl phenol monomer.

Preferred monomers used for the formation of such polymers include: an acid-labile monomer having the following formula (V), a lactone-containing monomer of the following formula (VI), a base-soluble monomer of the following formula (VII) for adjusting dissolution rate in alkaline developer, and an acid-generating monomer of the following formula (VIII), or a combination comprising at least one of the foregoing monomers:

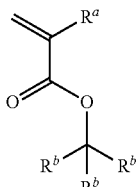
(V)

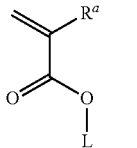
(VI)

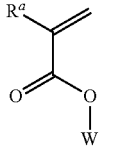
(VII)

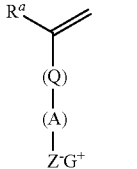
(VIII)

wherein each $R^a$ is independently H, F, —CN, $C_{1-10}$ alkyl, or $C_{1-10}$ fluoroalkyl. In the acid-deprotectable monomer of formula (V), $R^b$ is independently $C_{1-20}$ alkyl, $C_{3-20}$ cycloalkyl, $C_{6-20}$ aryl, or $C_{7-20}$ aralkyl, and each $R^b$ is separate or at least one $R^b$ is bonded to an adjacent $R^b$ to form a cyclic structure. In lactone-containing monomer of formula (VI), L is a monocyclic, polycyclic, or fused polycyclic $C_{4-20}$ lactone-containing group. In the base solubilizing monomer of formula (VII), W is a halogenated or non-halogenated, aromatic or non-aromatic $C_{2-50}$ hydroxyl-containing organic group having a pKa of less than or equal to 12. In the acid generating monomer of formula (VIII), Q is ester-containing or non-ester containing and fluorinated or non-fluorinated and is $C_{1-20}$ alkyl, $C_{3-20}$ cycloalkyl, $C_{6-20}$ aryl, or $C_{7-20}$ aralkyl group, A is ester-containing or non-ester containing and fluorinated or non-fluorinated, and is $C_{1-20}$ alkyl, $C_{3-20}$ cycloalkyl, $C_{6-20}$ aryl, or $C_{7-20}$ aralkyl, Z is an anionic moiety comprising carboxylate, sulfonate, an anion of a sulfonamide, or an anion of a sulfonimide, and $G^+$ is a sulfonium or iodonium cation.

Exemplary acid-deprotectable monomers include but are not limited to:

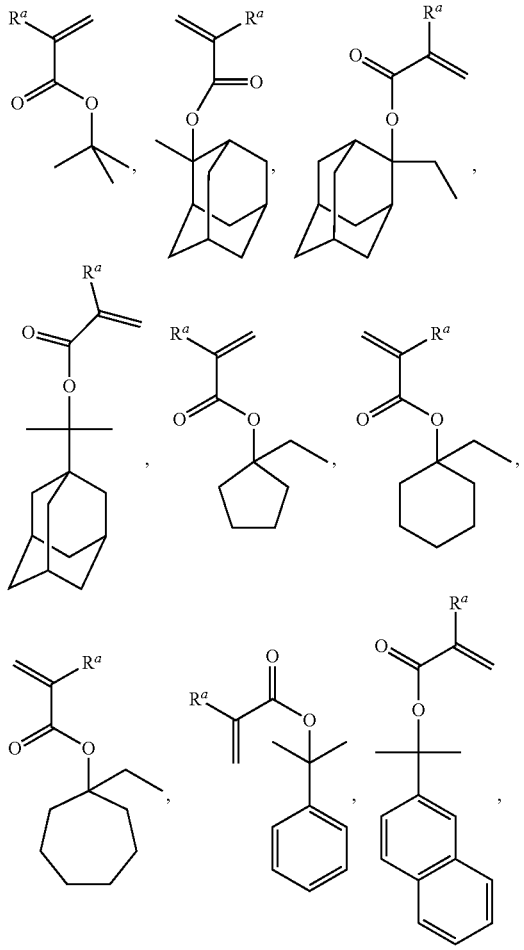

or a combination comprising at least one of the foregoing, wherein $R^a$ is H, F, —CN, $C_{1-6}$ alkyl, or $C_{1-6}$ fluoroalkyl.

Suitable lactone monomers may be of the following formula (IX):

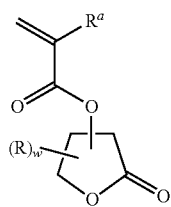

(IX)

wherein $R^a$ is H, F, —CN, $C_{1-6}$ alkyl, or $C_{1-6}$ fluoroalkyl, R is a $C_{1-10}$ alkyl, cycloalkyl, or heterocycloalkyl, and w is an integer of 0 to 5. In formula (IX), R is attached directly to the lactone ring or commonly attached to the lactone ring and/or one or more R groups, and the ester moiety is attached to the lactone ring directly, or indirectly through R.

Exemplary lactone-containing monomers include:

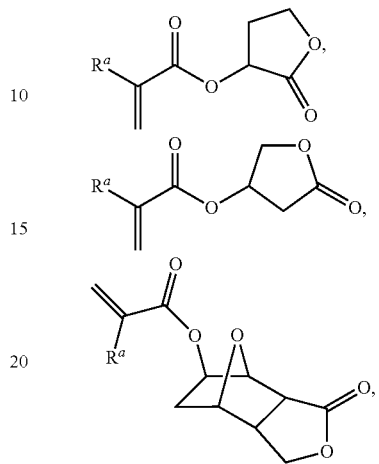

or a combination comprising at least one of the foregoing monomers, wherein $R^a$ is H, F, —CN, $C_{1-10}$ alkyl, or $C_{1-10}$ fluoroalkyl.

Suitable base-soluble monomers may be of the following formula (X):

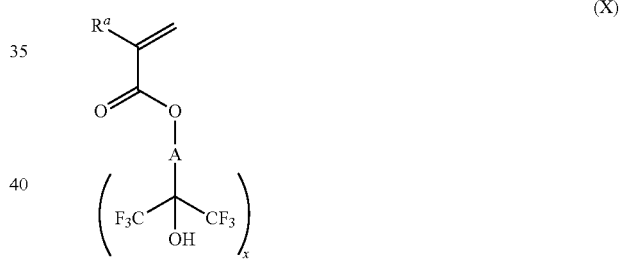

(X)

wherein each $R^a$ is independently H, F, —CN, $C_{1-10}$ alkyl, or $C_{1-10}$ fluoroalkyl, A is a hydroxyl-containing or non-hydroxyl containing, ester-containing or non ester-containing, fluorinated or non-fluorinated $C_{1-20}$ alkylene, $C_{3-20}$ cycloalkylene, $C_{6-20}$ arylene, or $C_{7-20}$ aralkylene, and x is an integer of from 0 to 4, wherein when x is 0, A is a hydroxyl-containing $C_{6-20}$ arylene.

Exemplary base soluble monomers include those having the following structures:

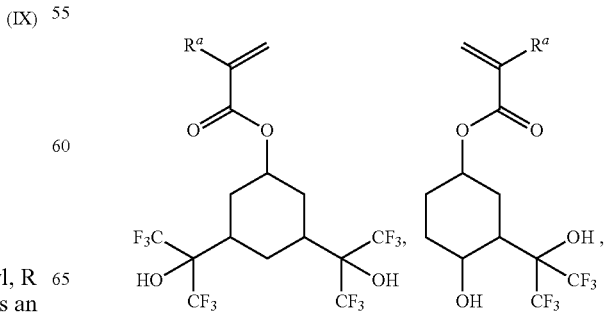

-continued

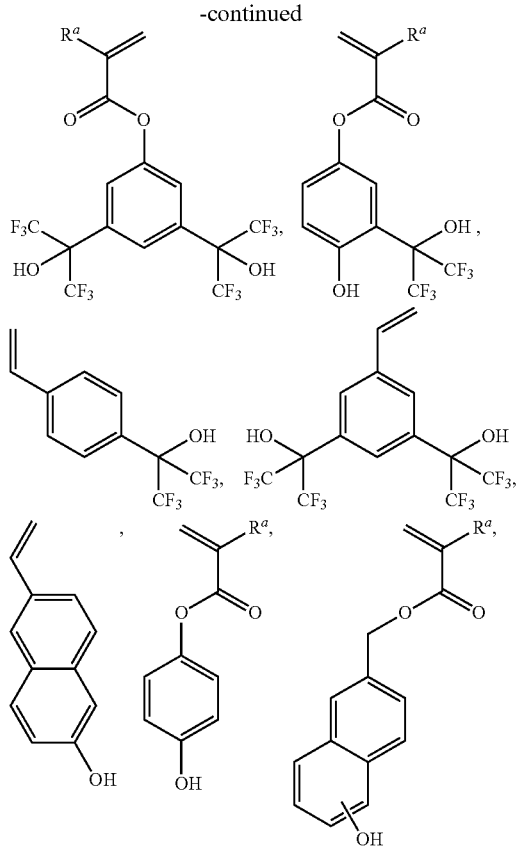

or a combination comprising at least one of the foregoing, wherein $R^a$ is H, F, —CN, $C_{1-6}$ alkyl, or $C_{1-6}$ fluoroalkyl.

Preferred acid generating monomers include those of the formulae (XI) or (XII):

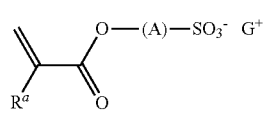     (XI)

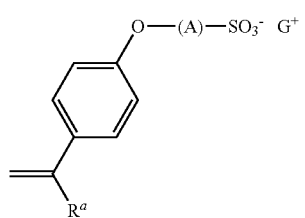     (XII)

wherein each $R^a$ is independently H, F, —CN, $C_{1-6}$ alkyl, or $C_{1-6}$ fluoroalkyl, A is a fluorine-substituted $C_{1-30}$ alkylene group, a fluorine-substituted $C_{3-30}$ cycloalkylene group, a fluorine-substituted $C_{6-30}$ arylene group, or a fluorine-substituted $C_{7-30}$ alkylene-arylene group, and $G^+$ is a sulfonium or iodonium cation.

Preferably, in formulas (XI) and (XII), A is a —[$C(R^1)_2$]$_x$C(=O)O]$_b$—C(($R^2)_2$)$_y$(CF$_2$)$_z$-group, or an o-, m- or p- substituted —$C_6F_4$-group, where each $R^1$ and $R^2$ are each independently H, F, —CN, $C_{1-6}$ fluoroalkyl, or $C_{1-6}$ alkyl, b is 0 or 1, x is an integer of 1 to 10, y and z are independently integers of from 0 to 10, and the sum of y+z is at least 1.

Exemplary preferred acid generating monomers include:

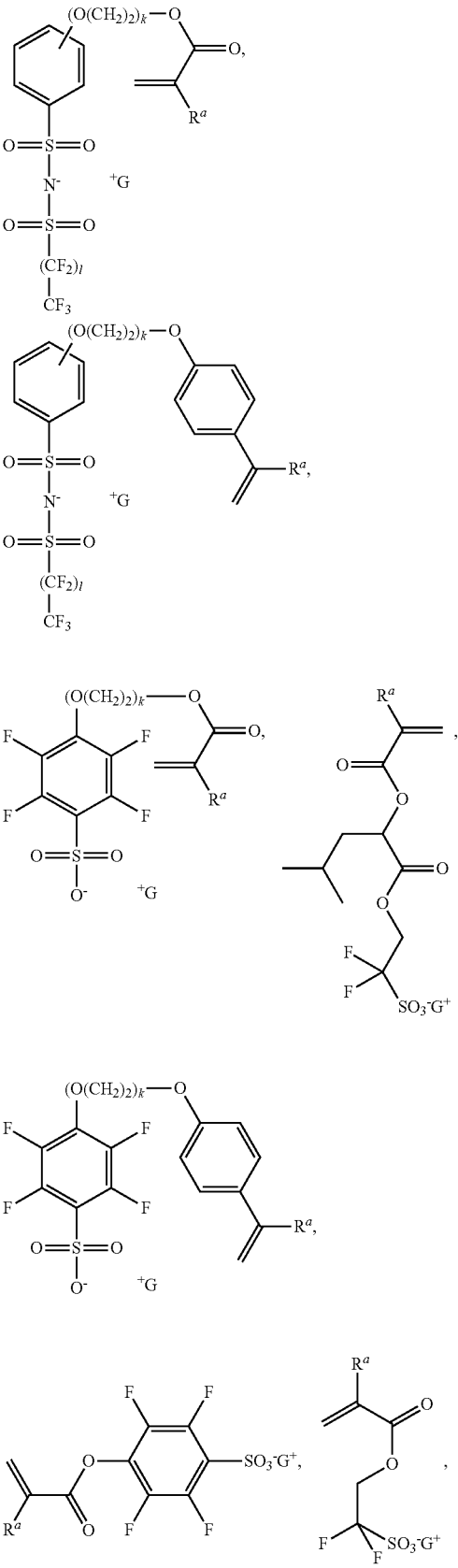

-continued

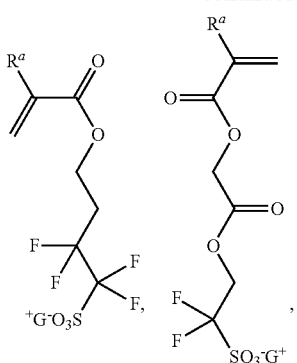

or a combination comprising at least one of the foregoing, where each $R^a$ is independently H, F, —CN, $C_{1-6}$ alkyl, or $C_{1-6}$ fluoroalkyl, k is suitably an integer of from 0 to 5; and $G^+$ is a sulfonium or iodonium cation. $G^+$ as referred to herein throughout the various formulae may be an acid generator as disclosed herein and comprise an oxo-dioxolane moiety and/or an oxo-dioxane moiety.

Preferred acid-generating monomers may include sulfonium or iodonium cation. Preferably, in formula (IV), $G^+$ is of the formula (XIII):

 (XIII)

wherein X is S or I, each $R^0$ is halogenated or non-halogenated and is independently $C_{1-30}$ alkyl group; a polycyclic or monocyclic $C_{3-30}$ cycloalkyl group; a polycyclic or monocyclic $C_{4-30}$ aryl group; or a combination comprising at least one of the foregoing, wherein when X is S, one of the $R^0$ groups is optionally attached to one adjacent $R^0$ group by a single bond, and a is 2 or 3, wherein when X is I, a is 2, or when X is S, a is 3.

Exemplary acid generating monomers include those having the formulas:

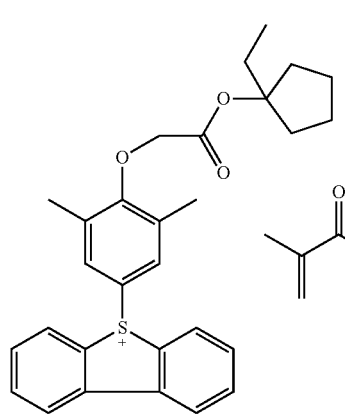

-continued

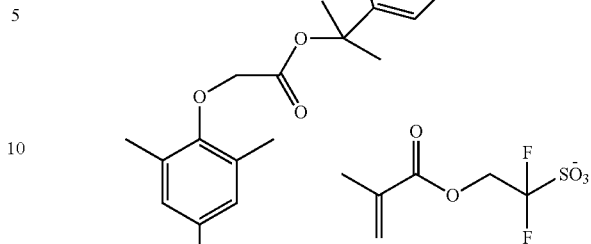

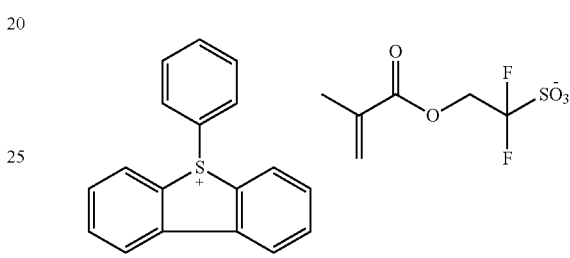

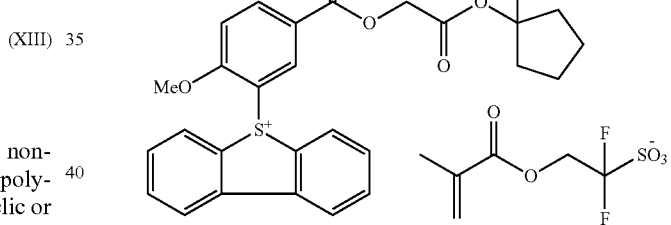

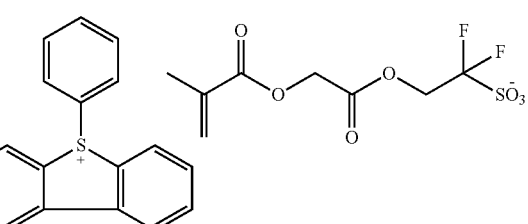

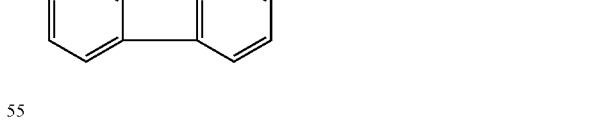

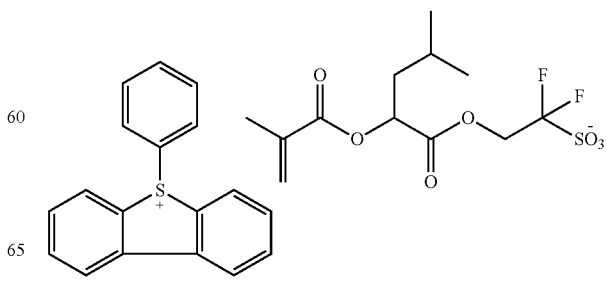

-continued

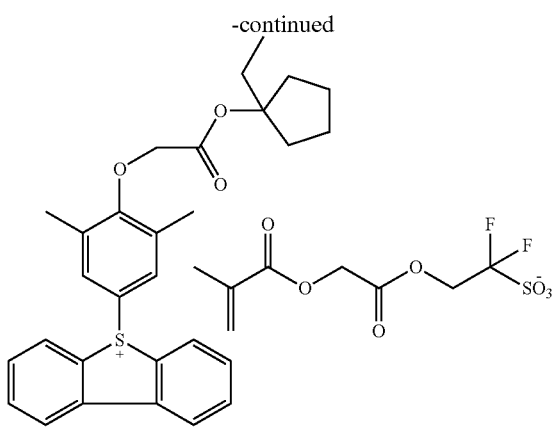

Specifically suitable polymers that have acid-labile deblocking groups for use in a positive-acting chemically-amplified photoresist of the invention have been disclosed in European Patent Application 0829766A2 (polymers with acetal and ketal polymers) and European Patent Application EP0783136A2 (terpolymers and other copolymers including units of 1) styrene; 2) hydroxystyrene; and 3) acid labile groups, particularly alkyl acrylate acid labile groups.

Additional preferred resins for use in photoresists to be imaged at sub-200 nm, such as at 193 nm, comprises units of the following general formulae (I), (II) and (III):

Preferred resins for use in photoresists to be imaged at sub-200 nm, such as at 193 nm, comprises units of the following general formulae (I), (II) and (III):

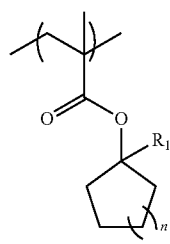 (I)

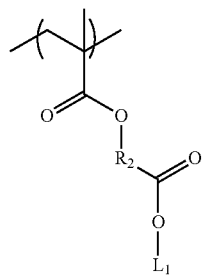 (II)

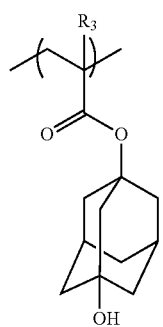 (III)

wherein: $R_1$ is a $(C_1-C_3)$alkyl group; $R_2$ is a $(C_1-C_3)$alkylene group; $L_1$ is a lactone group; and n is 1 or 2.

Polymers for use in photoresists of the invention may suitably vary widely in molecular weight and polydisperity. Suitable polymers include those that have an $M_w$ of from about 1,000 to about 50,000, more typically about 2,000 to about 30,000 with a molecular weight distribution of about 3 or less, more typically a molecular weight distribution of about 2 or less.

Preferred negative-acting compositions of the invention comprise a mixture of materials that will cure, crosslink or harden upon exposure to acid, and two or more acid generators as disclosed herein. Preferred negative acting compositions comprise a polymer binder such as a phenolic or non-aromatic polymer, a crosslinker component and a photoactive component of the invention. Such compositions and the use thereof have been disclosed in European Patent Applications 0164248 and U.S. Pat. No. 5,128,232 to Thackeray et al. Preferred phenolic polymers for use as the polymer binder component include novolaks and poly(vinylphenol)s such as those discussed above. Preferred crosslinkers include amine-based materials, including melamine, glycolurils, benzoguanamine-based materials and urea-based materials. Melamine-formaldehyde polymers are often particularly suitable. Such crosslinkers are commercially available, e.g. the melamine polymers, glycoluril polymers, urea-based polymer and benzoguanamine polymers, such as those sold by Cytec under tradenames Cymel 301, 303, 1170, 1171, 1172, 1123 and 1125 and Beetle 60, 65 and 80.

Particularly preferred photoresists of the invention may be used in immersion lithography applications. See, for example, U.S. Pat. No. 7,968,268 to Rohm and Haas Electronic Materials for a discussion of preferred immersion lithography photoresists and methods. Preferred photoresists for use in immersion application may comprise a resin (which may be fluorinated and/or have acid-labile groups) that is separate (not covalently linked) and distinct from a primary resin that has photoacid-labile groups. Thus, the present invention includes in preferred aspects photoresists that comprise: 1) a first resin with acid-labile groups; 2) one or more acid generator compounds; 3) a second resin that is separate and distinct from the first resin, the second resin may be fluorinated and/or have acid-labile groups; and 4) one or more photobase generator compounds as disclosed herein.

Photoresists of the invention also may comprise a single acid generator or a mixture of distinct acid generators, typically a mixture of 2 or 3 different acid generators, more typically a mixture that consists of a total of 2 distinct acid generators. The photoresist composition comprises an acid generator employed in an amount sufficient to generate a latent image in a coating layer of the composition upon exposure to activating radiation. For example, the acid generator will suitably be present in an amount of from 1 to 20 wt % based on total solids of the photoresist composition. Typically, lesser amounts of the acid generator be suitable for chemically amplified resists as compared with non-chemically amplified materials.

Suitable acid generators are known in the art of chemically amplified photoresists and include, for example: onium salts, for example, triphenylsulfonium trifluoromethanesulfonate, (p-tert-butoxyphenyl)diphenylsulfonium trifluoromethanesulfonate, tris(p-tert-butoxyphenyl)sulfonium trifluoromethanesulfonate, triphenylsulfonium p-toluenesulfonate; nitrobenzyl derivatives, for example, 2-nitrobenzyl-p-toluenesulfonate, 2,6-dinitrobenzyl-p-toluenesulfonate, and 2,4-dinitrobenzyl-p-toluenesulfonate; sulfonic acid esters, for example, 1,2,3-tris(methanesulfonyloxy)benzene, 1,2,3-tris(trifluoromethanesulfonyloxy) benzene, and 1,2,3-tris(p-toluenesulfonyloxy)benzene; diazomethane derivatives, for example, bis(benzenesulfonyl)diazomethane, bis(p-toluenesulfonyl)diazomethane; glyoxime derivatives, for example, bis-O-(p-toluenesulfonyl)-α-dimethylglyoxime, and bis-O-(n-butanesulfonyl)-α-dimethylglyoxime; sulfonic acid ester derivatives of an N-hydroxyimide compound, for example, N-hydroxysuccinimide methanesulfonic acid ester, N-hydroxysuccinimide trifluoromethanesulfonic acid ester; and halogen-containing triazine compounds, for example, 2-(4-methoxyphenyl)-4, 6-bis(trichloromethyl)-1,3,5-triazine, and 2-(4-methoxynaphthyl)-4,6-bis(trichloromethyl)-1,3,5-triazine.

As referred to herein, acid generators can produce an acid when exposed to activating radiation, such as EUV radiation, e-beam radiation, 193 nm wavelength radiation or other radiation sources. Acid generator compounds as referred to herein also may be referred to as photoacid generator compounds.

Photoresists of the invention suitably may comprise one or more photobase generator compounds as disclosed herein in a wide amount range, such as from 0.005 to 15 wt %, based on the weight of the acid generator, preferably from 0.01 to 15 wt %, and even more preferably from 0.01 to 10 wt %. The added photobase generator component is suitably used in amounts of 0.01, 0.05, 0.1, 0.02, 0.3, 0.4, 0.5 or 1 to 10 or 15 wt % relative to the acid generator, and more typically amounts of 0.01, 0.05, 0.1, 0.02, 0.3, 0.4, 0.5 or 1 to 5, 6, 7, 8, 9 or 10 weight percent.

Photoresists of the invention also may contain other materials. For example, other optional additives include actinic and contrast dyes, anti-striation agents, plasticizers, speed enhancers and sensitizers. Such optional additives typically will be present in minor concentration in a photoresist composition.

Alternatively, or in addition, other additives may include quenchers that are non-photo-destroyable bases, such as, for example, those based on hydroxides, carboxylates, amines, imines, and amides. Preferably, such quenchers include $C_{1-30}$ organic amines, imines, or amides, or may be a $C_{1-30}$ quaternary ammonium salt of a strong base (e.g., a hydroxide or alkoxide) or a weak base (e.g., a carboxylate). Exemplary quenchers include amines such as tripropylamine, dodecylamine, tris(2-hydroxypropyl)amine, oltetrakis (2-hydroxypropyl)ethylenediamine; aryl amines such as diphenylamine, triphenylamine, aminophenol, and 2-(4-aminophenyl)-2-(4-hydroxyphenyl)propane, Troger's base, a hindered amine such as diazabicycloundecene (DBU) or diazabicyclononene (DBN), or ionic quenchers including quaternary alkyl ammonium salts such as tetrabutylammonium hydroxide (TBAH) or tetrabutylammonium lactate.

Surfactants include fluorinated and non-fluorinated surfactants, and are preferably non-ionic. Exemplary fluorinated non-ionic surfactants include perfluoro $C_4$ surfactants such as FC-4430 and FC-4432 surfactants, available from 3M Corporation; and fluorodiols such as POLYFOX PF-636, PF-6320, PF-656, and PF-6520 fluorosurfactants from Omnova.

The photoresist further includes a solvent generally suitable for dissolving, dispensing, and coating the components used in a photoresists. Exemplary solvents include anisole, alcohols including ethyl lactate, 1-methoxy-2-propanol, and 1-ethoxy-2 propanol, esters including n-butylacetate, 1-methoxy-2-propyl acetate, methoxyethoxypropionate, ethoxyethoxypropionate, ketones including cyclohexanone and 2-heptanone, and a combination comprising at least one of the foregoing solvents.

Such photoresists may include the polymer in an amount of 50 to 99 wt %, specifically 55 to 95 wt %, more specifically 60 to 90 wt %, and still more specifically 65 to 90 based on the total weight of solids. The photo-destroyable base may be present in the photoresist in an amount of 0.01 to 5 wt %, specifically 0.1 to 4 wt %, and still more specifically 0.2 to 3 wt %, based on the total weight of solids. A surfactant may be included in an amount of 0.01 to 5 wt %, specifically 0.1 to 4 wt %, and still more specifically 0.2 to 3 wt %, based on the total weight of solids. A quencher may be included in relatively small amounts of for example, from 0.03 to 5 wt % based on the total weight of solids. Other additives may be included in amounts of less than or equal to 50 wt %, specifically less than or equal to 35%, or more specifically less than or equal to 25%, based on the total weight of solids. The total solids content for the photoresist composition may be 0.5 to 50 wt %, specifically 1 to 45 wt %, more specifically 2 to 40 wt %, and still more specifically 5 to 30 wt %, based on the total weight of solids and solvent. The acid generators should be present in an amount sufficient to enable generation of a latent image in a coating layer of the resist. More specifically, the two or more acid generators will suitably be present in an amount of from about 1 to 50 weight percent of total solids of a resist. It will be understood that the solids includes polymer, quencher, surfactant, and any optional additives, exclusive of solvent.

A coated substrate may be formed from the photoresist containing acid generators which should be present in an amount sufficient to enable generation of a latent image in a coating layer of the resist and acid generators. Such a coated substrate includes: (a) a substrate having one or more layers to be patterned on a surface thereof; and (b) a layer of the photoresist composition including the acid generator over the one or more layers to be patterned. For EUV or e-beam imaging, photoresists may suitably have relatively higher content of acid generator compounds, e.g. where the one or more acid generators comprise 5 to 10 to about 65 weight percent of total solids of the resist. Typically, lesser amounts of the photoactive component will be suitable for chemically amplified resists.

The photoresists of the invention are generally prepared following known procedures with the exception that one or more acid generator compounds of the invention are substituted for prior photoactive compounds used in the formulation of such photoresists. The photoresists of the invention can be used in accordance with known procedures.

Substrates may be any dimension and shape, and are preferably those useful for photolithography, such as silicon, silicon dioxide, silicon-on-insulator (SOI), strained silicon, gallium arsenide, coated substrates including those coated with silicon nitride, silicon oxynitride, titanium nitride, tantalum nitride, ultrathin gate oxides such as hafnium oxide, metal or metal coated substrates including those coated with titanium, tantalum, copper, aluminum, tungsten, alloys thereof, and combinations thereof. Preferably, the surfaces of substrates herein include critical dimension layers to be patterned including, for example, one or more gate-level layers or other critical dimension layer on the substrates for semiconductor manufacture. Such substrates may preferably include silicon, SOI, strained silicon, and other such substrate materials, formed as circular wafers having dimensions such as, for example, 20 cm, 30 cm, or larger in diameter, or other dimensions useful for wafer fabrication production.

Further, a method of forming an electronic device includes (a) applying a layer of a photoresist composition including on a surface of the substrate; (b) patternwise exposing the photoresist composition layer to activating radiation; and (c) developing the exposed photoresist composition layer to provide a resist relief image.

Applying may be accomplished by any suitable method, including spin coating, spray coating, dip coating, doctor blading, or the like. Applying the layer of photoresist is preferably accomplished by spin-coating the photoresist in solvent using a coating track, in which the photoresist is dispensed on a spinning wafer. During dispense, the wafer may be spun at a speed of up to 4,000 rpm, preferably from about 500 to 3,000 rpm, and more preferably 1,000 to 2,500 rpm. The coated wafer is spun to remove solvent, and baked on a hot plate to remove residual solvent and free volume from the film to make it uniformly dense.

Patternwise exposure is then carried out using an exposure tool such as a stepper, in which the film is irradiated through a pattern mask and thereby is exposed pattern-wise. The method preferably uses advanced exposure tools generating activating radiation at wavelengths capable of high resolution including extreme-ultraviolet (EUV) or e-beam radiation. It will be appreciated that exposure using the activating radiation decomposes the acid generator in the exposed areas and generates acid and decomposition by-products, and that the acid then effects a chemical change in the polymer (deblocking the acid sensitive group to generate a base-soluble group, or alternatively, catalyzing a cross-linking reaction in the exposed areas). The resolution of such exposure tools may be less than 30 nm.

Developing the exposed photoresist layer is then accomplished by treating the exposed layer to a suitable developer capable of selectively removing the exposed portions of the film (where the photoresist is positive tone) or removing the unexposed portions of the film (where the photoresist is crosslinkable in the exposed regions, i.e., negative tone). Preferably, the photoresist is positive tone based on a polymer having acid sensitive (deprotectable) groups, and the developer is preferably a metal-ion free tetraalkylammonium hydroxide solution, such as, for example, aqueous 0.26 N tetramethylammonium hydroxide. A pattern forms by developing.

Additionally, for positive resists, unexposed regions can be selectively removed by treatment with a suitable nonpolar solvent for negative tone development. See U.S. 2011/0294069 for suitable procedures for negative tone development of positive photoresists. Typical nonpolar solvents for negative tone development are organic developers, such as a solvent chosen from ketones, esters, hydrocarbons, and mixtures thereof, e.g. acetone, 2-hexanone, methyl acetate, butyl acetate, and tetrahydrofuran.

The photoresist may, when used in one or more such a pattern-forming processes, be used to fabricate electronic and optoelectronic devices such as memory devices, processor chips (CPU's), graphics chips, and other such devices.

The following non-limiting examples are illustrative of the invention.

Example 1: Synthesis of NB-DiOC(C)

Scheme 1.

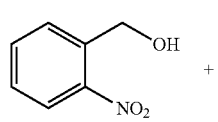

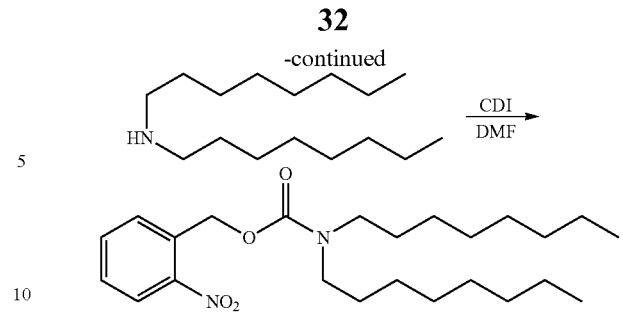

As generally depicted in the above Scheme 1, 1,1'-Carbonyldiimidazole(5.3 g; 1.0 eq.) was suspended in anhydrous DMF(60 mL) under nitrogen atmosphere. The solution was cooled to 0° C. and (2-nitrophenyl)methanol (5.0 g; 1.0 eq.) in anhydrous DMF(40 mL) was slowly added. After stirring at RT for 3 h, dioctylamine (7.88 g; 1.0 eq.) was added. The mixture was stirred at 70° C. for 20 h. The reaction mixture was diluted with EA, washed water. The organic phase is dried over sodium sulfate, filtered off and concentrated under reduced pressure. The crude compound of the title compound was purified by flash chromatography (EtOAc/heptane).

Example 2: Synthesis of NB-DEHC(E)

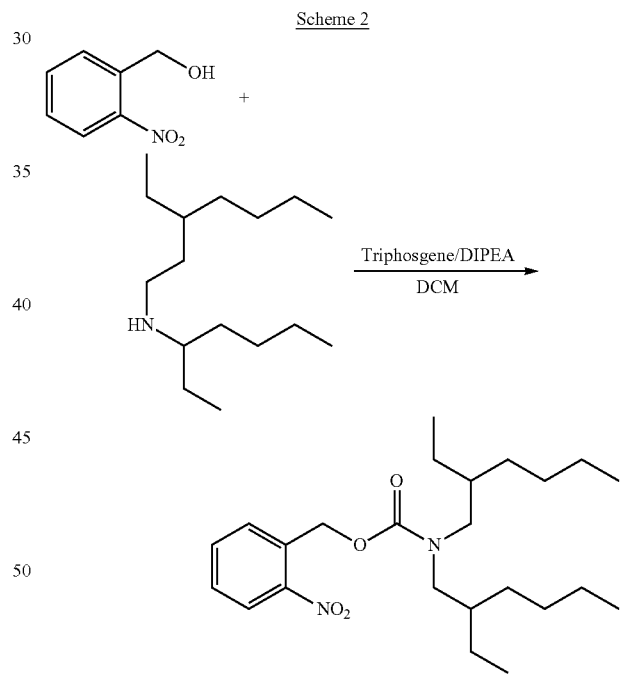

As generally depicted in the above Scheme 2, Triphosgene(1.16 g 0.3 eq.) suspended in anhydrous DCM(30 mL) under nitrogen atmosphere. The solution was cooled to 0° C. Then (2-nitrophenyl)methanol (2.0 g; 1.0 eq.) in anhydrous DCM(30 mL) and N,N-diisopropylethylamine (3.38 g; 2.0 eq.) were added. After stirring at RT for 3 h, bis(2-ethylhexyl)amine (3.15 g; 1.0 eq.) was slowly added and stirred for 4 h. The reaction mixture was washed by water and the organic phase is dried over sodium sulfate, filtered off and concentrated under reduced pressure. The crude title compound was purified by flash chromatography (EtOAc/heptane).

Example 3: Synthesis of ANT-DEHC

Scheme 3

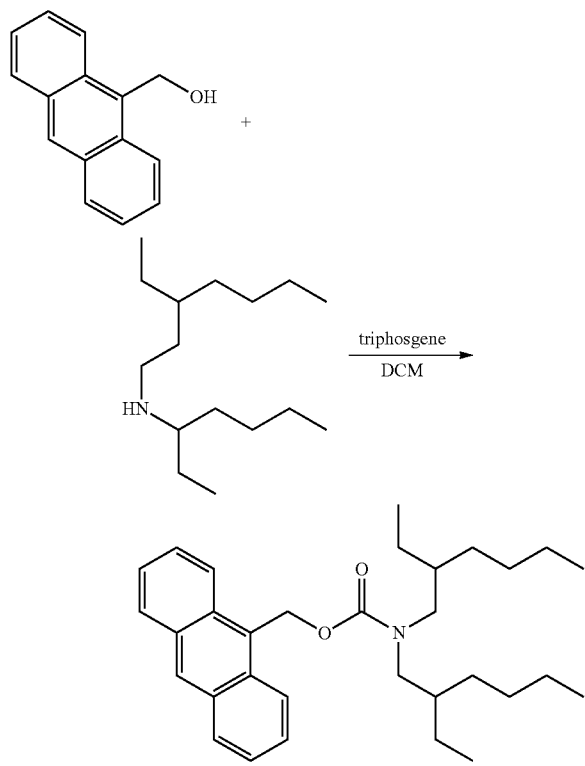

As generally depicted in Scheme 3 above, triphosgene (2.137 g 0.5 eq.) suspended in anhydrous DCM(30 mL) under nitrogen atmosphere. The solution was cooled to 0° C. Then 9-(Hydroxymethyl)anthracene(3.0 g; 1.0 eq.) in anhydrous DCM(100 mL) and N,N-diisopropylethylamine(3.723 g; 2.0 eq.) were added. After stirring at RT for 3 h, bis(2-ethylhexyl)amine(3.478 g; 1.0 eq.) was slowly added and stirred for 4 h. The reaction mixture was washed by water and the organic phase is dried over sodium sulfate, filtered off and concentrated under reduced pressure. The crude title compound was purified by flash chromatography(EtOAc/heptane).

Example 4: Preparation of Photoresist Composition

A photoresist composition of the invention is prepared by admixing the following components, 13.34 g polymer-A solution(20%) in PGMEA, 15.22 g PAG-A solution(1%) in methyl-2-hydroxyisobutyrate, 5.34 g PAG-B solution(2%) in methyl-2-Hydroxyisobutyrate, 3.53 g WPAG solution (2%) in methyl-2-hydroxyisobutyrate, 3.57 g Quencher-A solution(1%) in PGMEA, 0.43 g PBG A solution(1%) in methyl-2-Hydroxyisobutyrate, 1.24 g EBL(5%) in PGMEA, 33.07 g PGMEA, 9.69 g gamma-butyrolactone and 14.57 g methyl-2-hydroxyisobutyrate and then this mixture was filtered with a 0.2 micron Nylon filter. Polymer-A, PAG-A, PAG-B, WAG, Quencher-A, EBL and PBG A of this photoresist composition have the following structures:

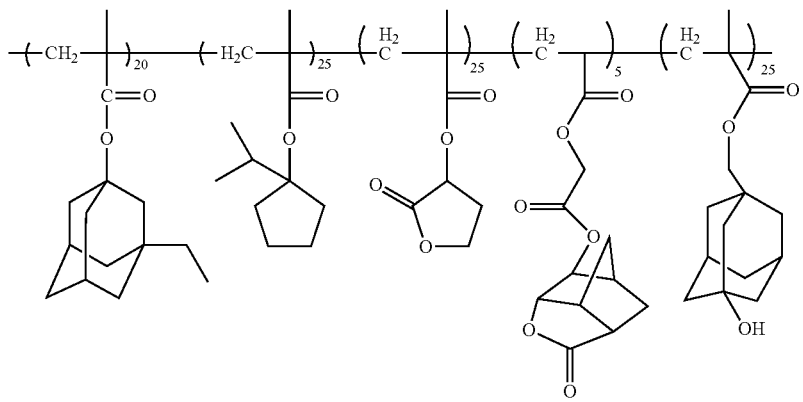

EAMA/IPCPMA/aGBLMA/MNLMA/HAMA
(20/25/25/5/25)
Polymer-A

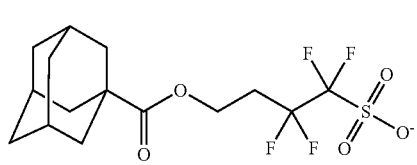

PAG-A

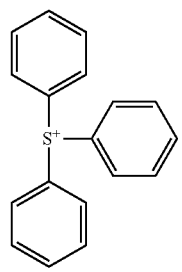

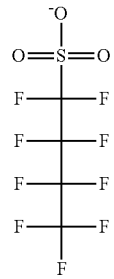

PAG-B

-continued

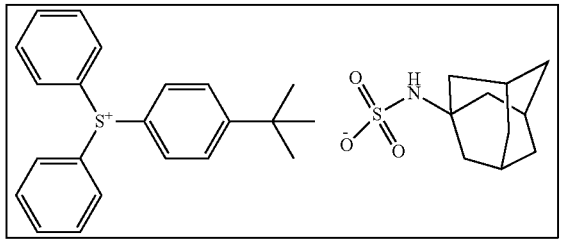

WPAG

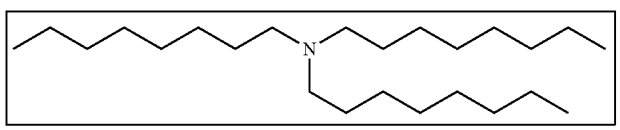

Quencher-A

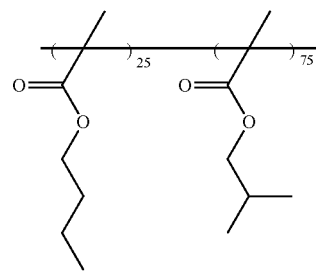

EBL

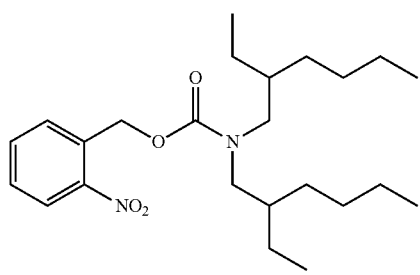

PBG A

Example 5: Preparation of Photoresist Composition

A photoresist composition of the invention is prepared by admixing the following components, 13.27 g polymer-A solution(20%) in PGMEA, 15.98 g PAG-A solution(1%) in methyl-2-hydroxyisobutyrate, 5.60 g PAG-B solution(2%) in methyl-2-Hydroxyisobutyrate, 3.53 g WPAG solution (2%) in methyl-2-hydroxyisobutyrate, 3.92 g Quencher-A solution(1%) in PGMEA, 0.31 g PBG B solution(1%) in methyl-2-Hydroxyisobutyrate, 1.24 g EBL(5%) in PGMEA, 32.78 g PGMEA, 9.69 g gamma-butyrolactone and 13.67 g methyl-2-hydroxyisobutyrate and then this mixture was filtered with a 0.2 micron Nylon filter. Polymer-A, PAG-A, PAG-B, WAG, Quencher-A, EBL and PBG A of this photoresist composition have the following structures:

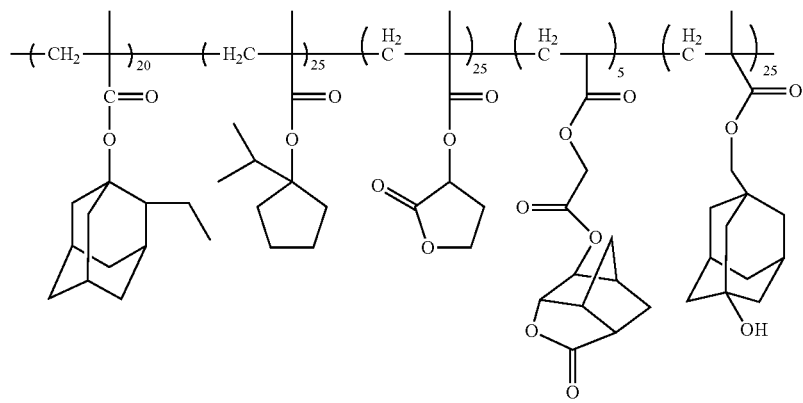
EAMA/IPCPMA/aGBLMA/MNLMA/HAMA
(20/25/25/5/25)
Polymer-A
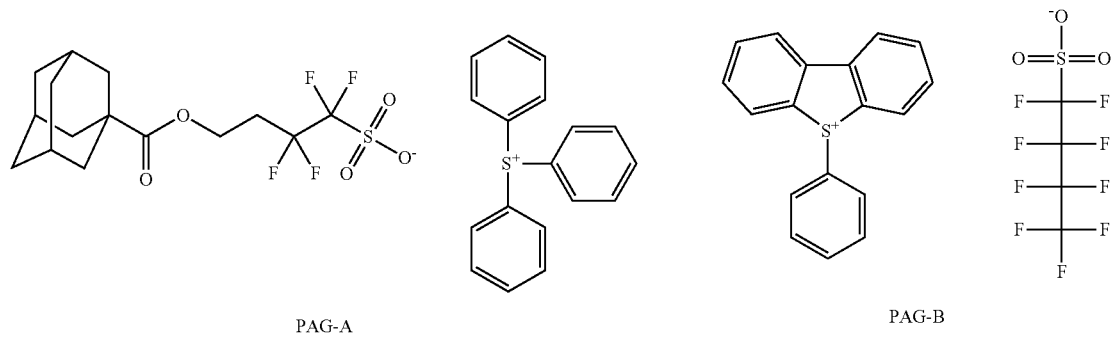
PAG-A
PAG-B
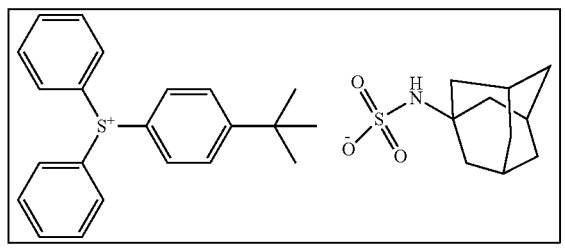
WPAG
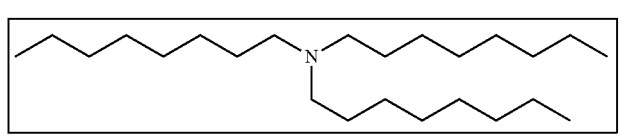
Quencher-A
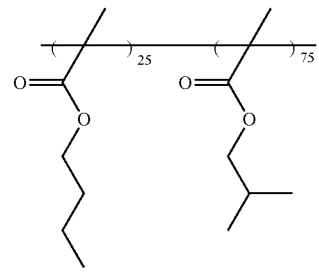
EBL

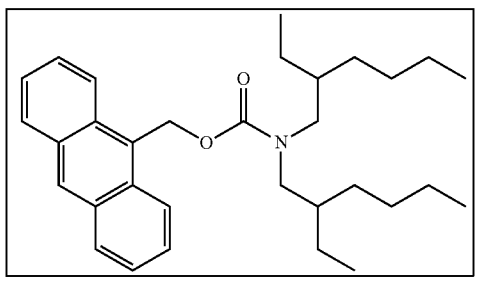

PBG B

Example 6: Lithography 300 mm HMDS-primed silicon wafers are spin-coated with AR™26N (Rohm and Haas Electronic Materials) to form a first bottom anti-reflective coating (BARC) on a TEL CLEAN TRAC LITHIUS i+, followed by the bake process for 60 seconds at 205° C.

A photoresist composition of Example 4 is spin-coated over the BARC layer. The thus applied photoresist layer is then soft-baked and imaged in an immersion lithography system with patterned radiation having a wavelength of 193 nm. The exposed wafers are post-exposure baked at 90° C. for 60 seconds and then developed using n-butyl acetate developer for approximately 30 seconds to give negative tone patterns of the photoresist.

Example 7: Lithography 300 mm HMDS-primed silicon wafers are spin-coated with AR™26N (Rohm and Haas Electronic Materials) to form a first bottom anti-reflective coating (BARC) on a TEL CLEAN TRAC LITHIUS i+, followed by the bake process for 60 seconds at 205° C.

A photoresist composition of Example 5 is spin-coated over the BARC layer. The thus applied photoresist layer is then soft-baked and imaged in an immersion lithography system with patterned radiation having a wavelength of 193 nm. The exposed wafers are post-exposure baked at 90° C. for 60 seconds and then developed using n-butyl acetate developer for approximately 30 seconds to give negative tone patterns of the photoresist.

What is claimed is:

1. A method for forming a photolithographic pattern, comprising:
   (a) applying a layer of a positive-acting photoresist composition on a substrate, the photoresist composition comprising (1) a resin comprising photoacid-labile groups; (2) one or more acid generators; and (3) a photobase generator that corresponds to the following Formula (IA):

$$X_1-(CYZ)_n-O-C(=O)N(R_2)R_3 \qquad (IA)$$

wherein $X_1$ is an optionally substituted aromatic group;
   each Y and Z is independently hydrogen or a non-hydrogen substituent;
   n is a positive integer; and
   $R_2$ and $R_3$ are the same or different, optionally substituted branched alkyl group having 4 or more carbon atoms; and
   (b) patternwise exposing the photoresist composition layer to activating radiation; and
   (c) developing the exposed photoresist composition layer to provide a photoresist relief image.

2. The method of claim 1 wherein $X_1$ is optionally substituted anthracenyl or phenyl.

3. The method of claim 1 wherein $R_2$ and $R_3$ are each independently optionally substituted branched alkyl having 6 or more carbon atoms.

4. The method of claim 1 wherein $R_2$ and/or $R_3$ are fluorinated branched alkyl having 4 or more carbon atoms.

5. The method of claim 1 wherein the photobase generator is selected from among the following:

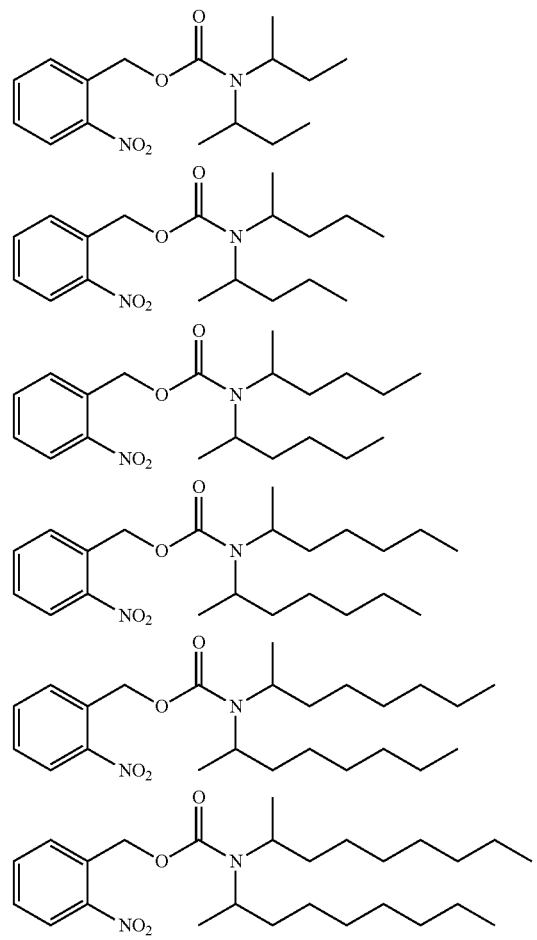

41
-continued
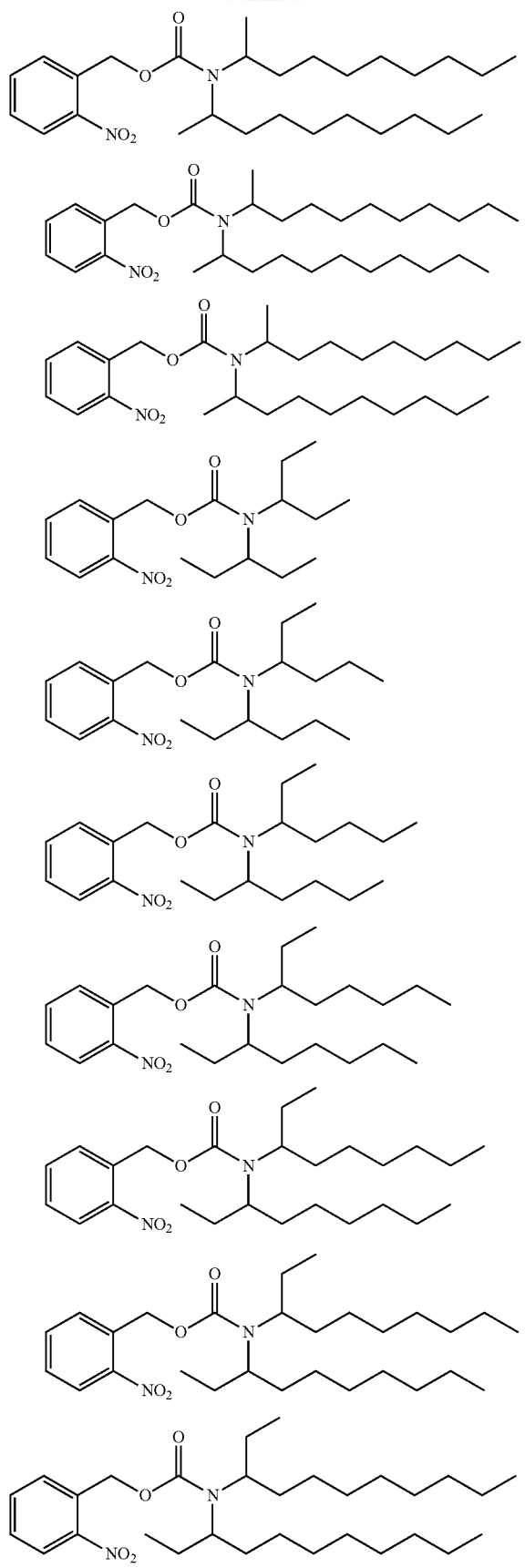
42
-continued
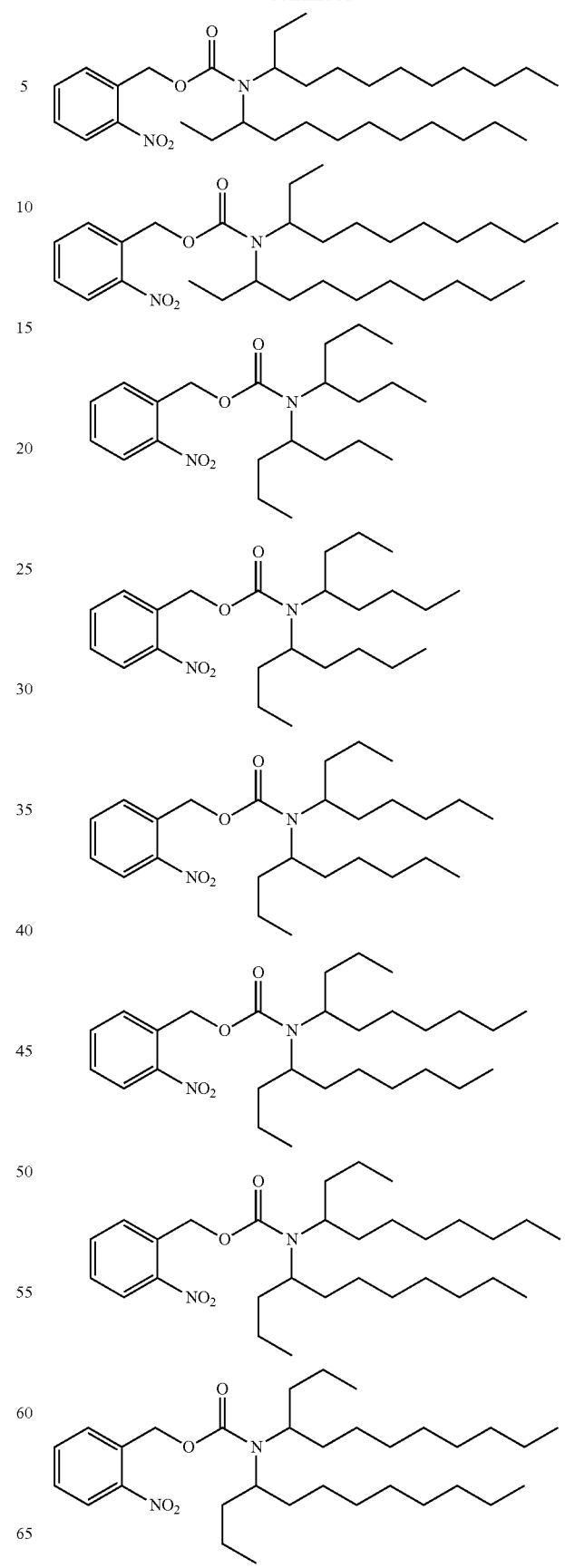

-continued
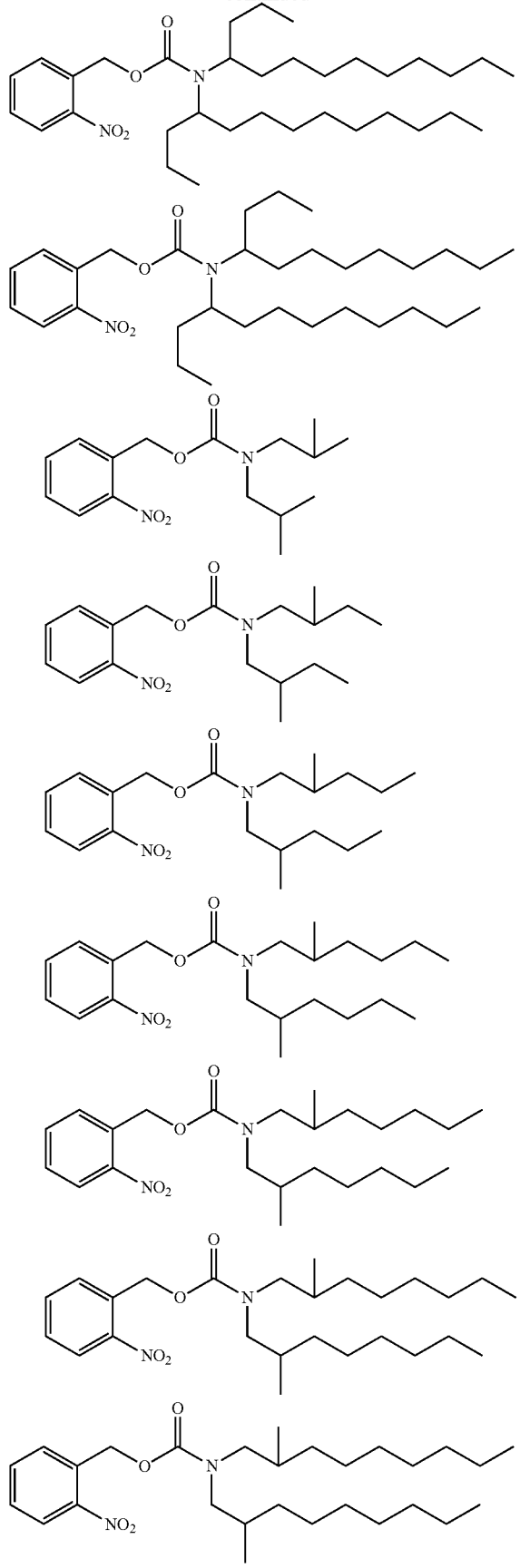
-continued
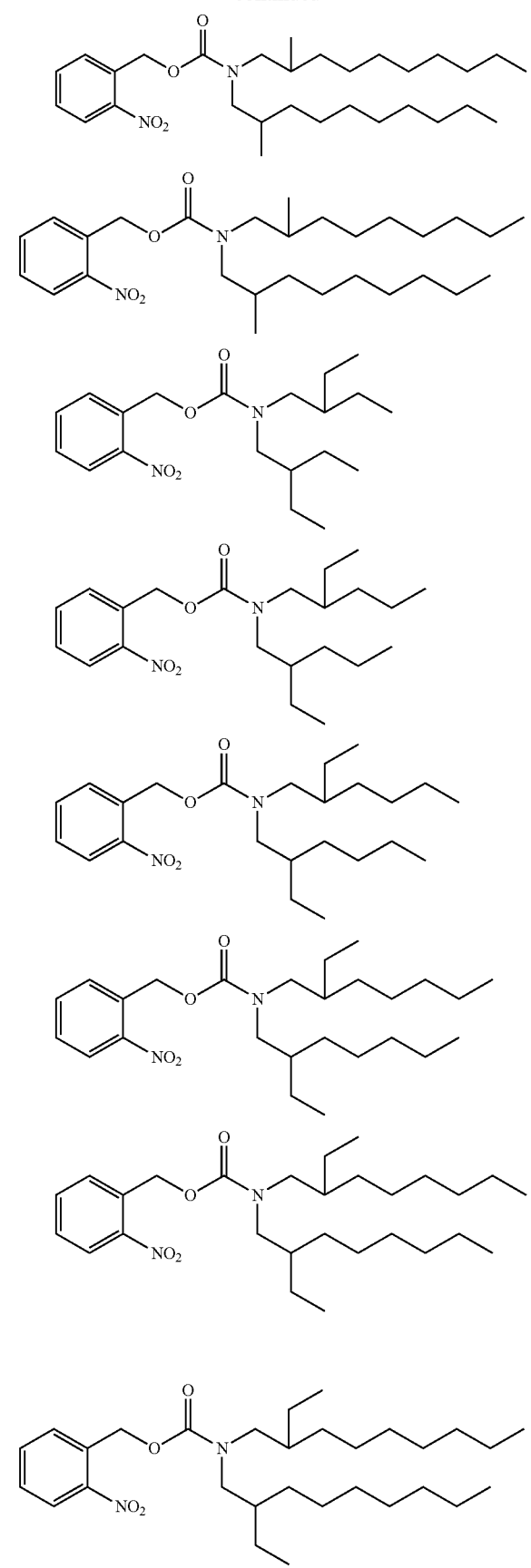

45
-continued
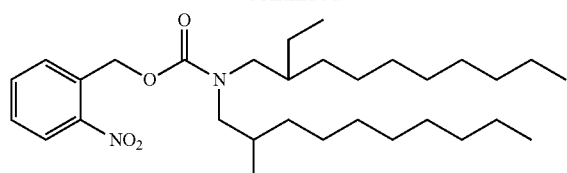
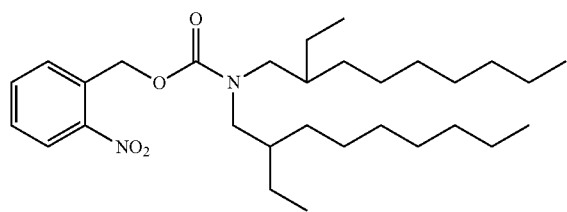
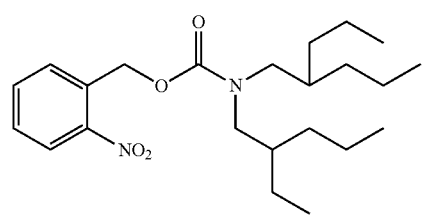
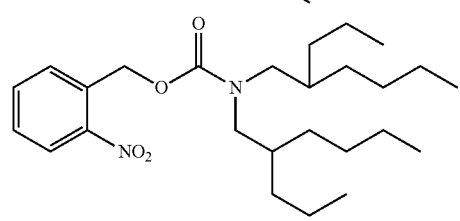
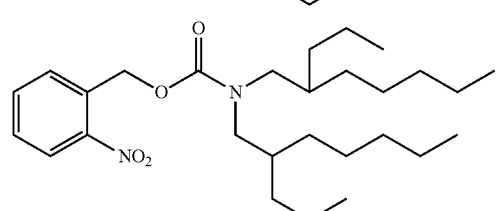
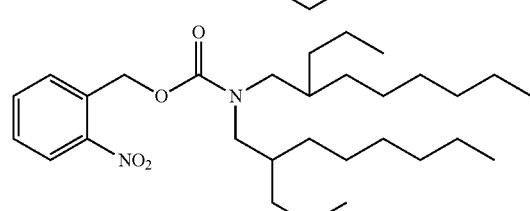
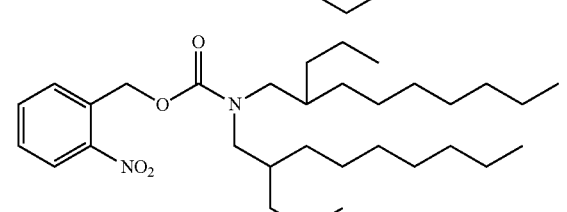
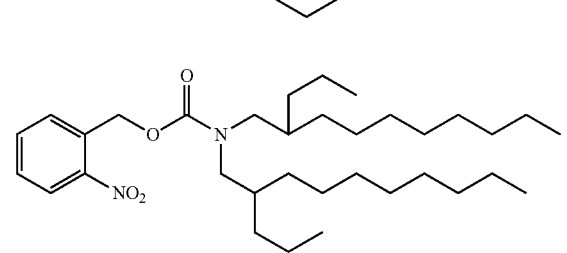
46
-continued
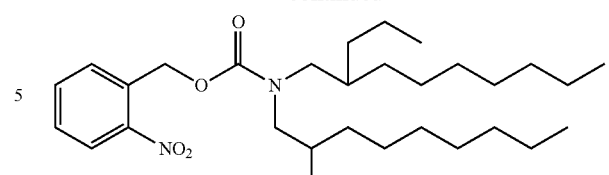
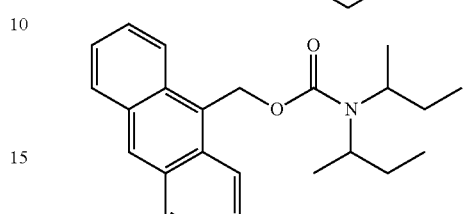
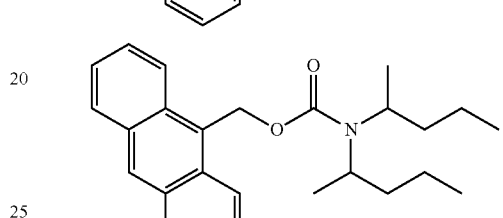
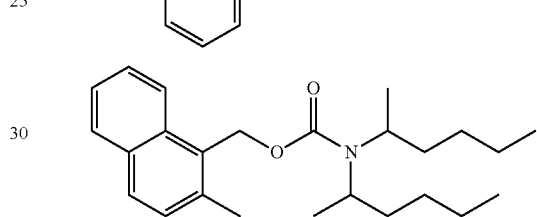
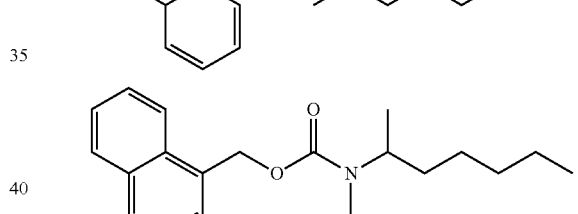
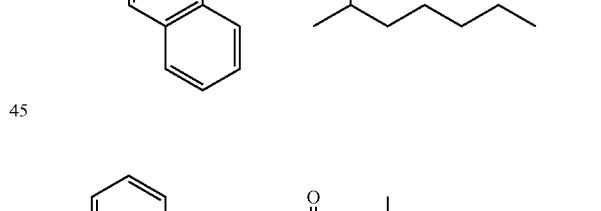
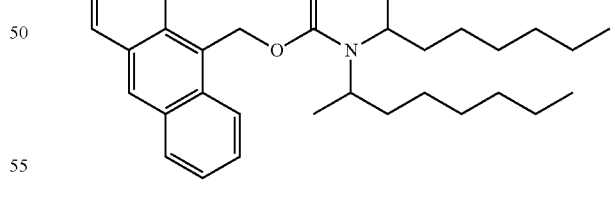
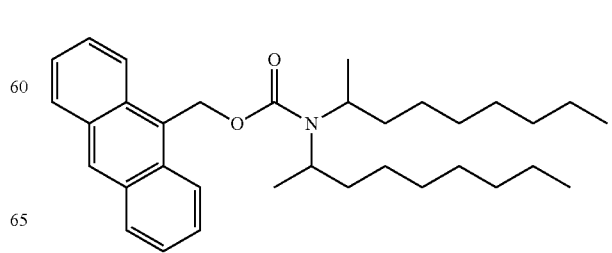

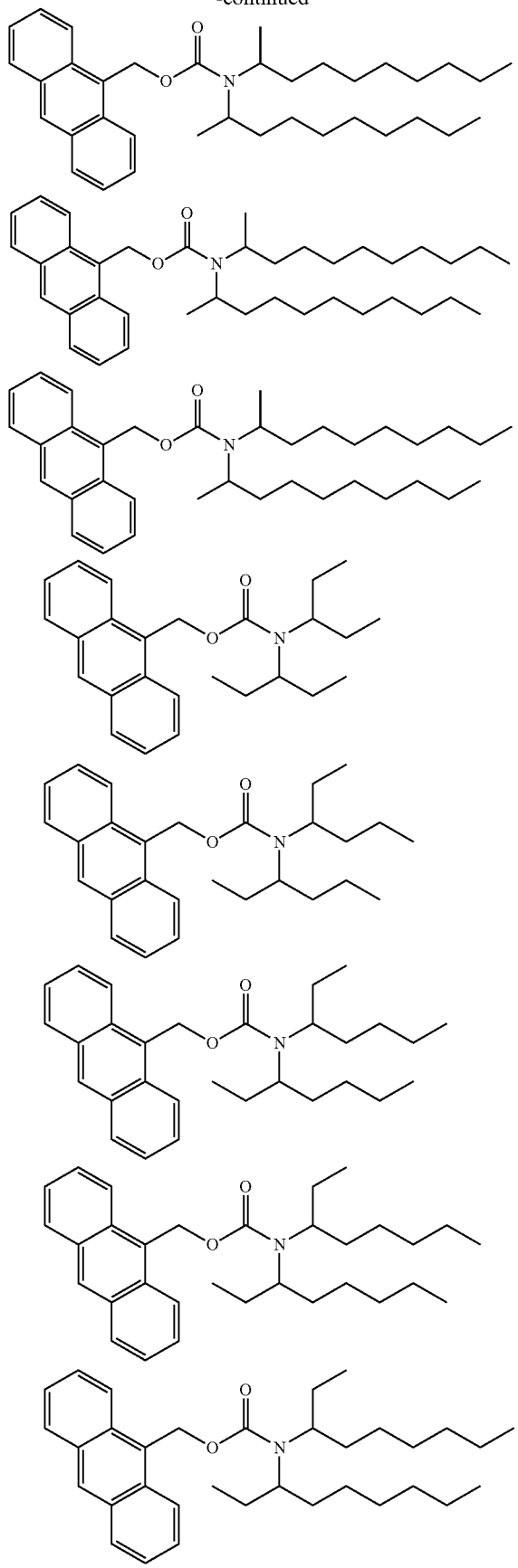
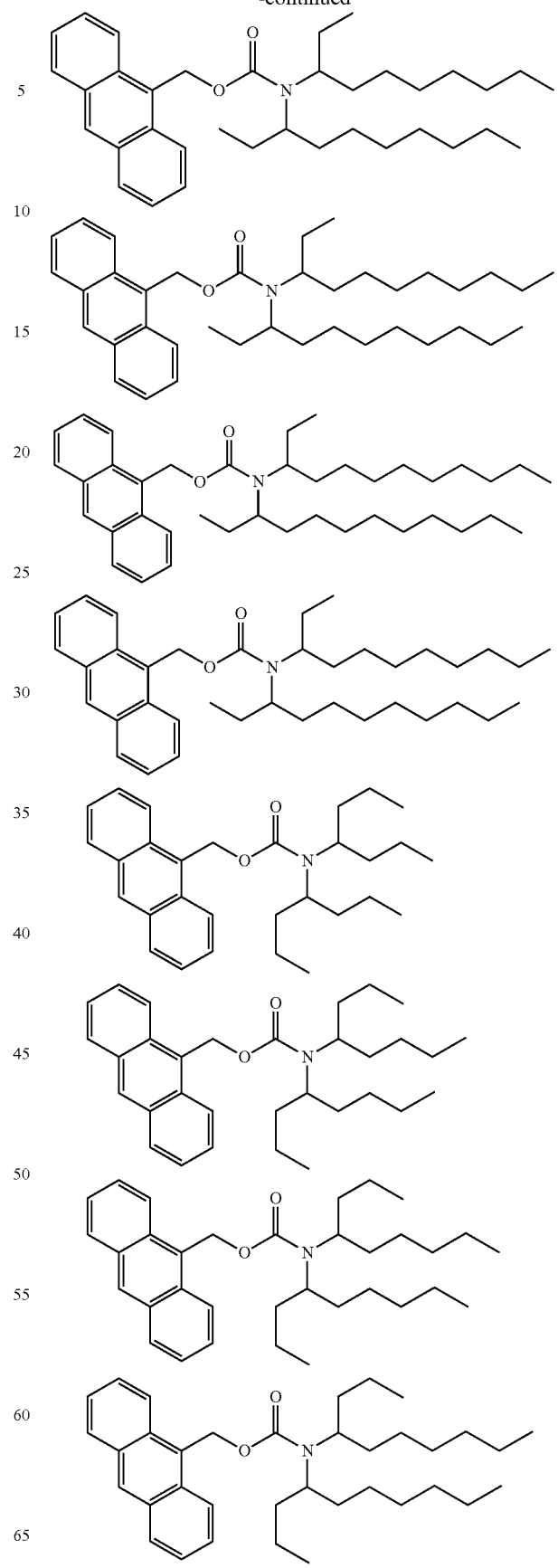

49
-continued
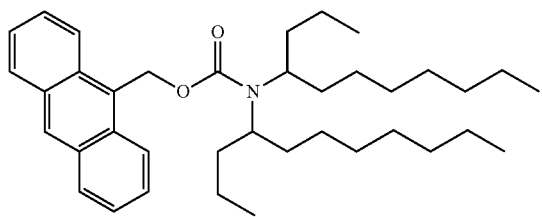
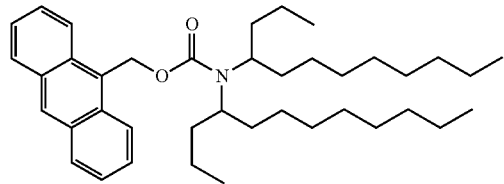
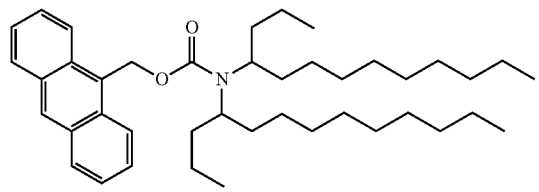
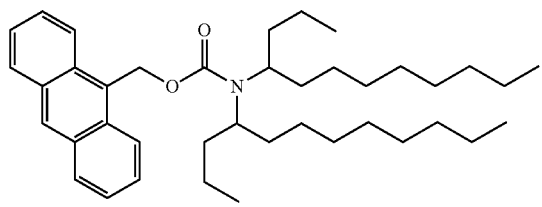
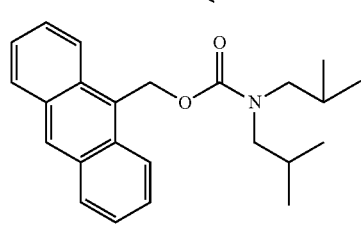
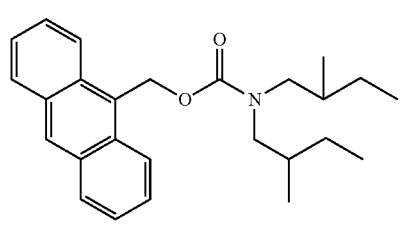
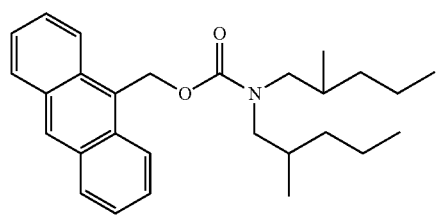
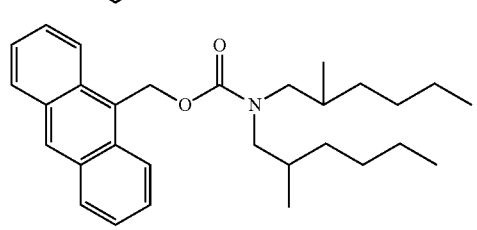
50
-continued
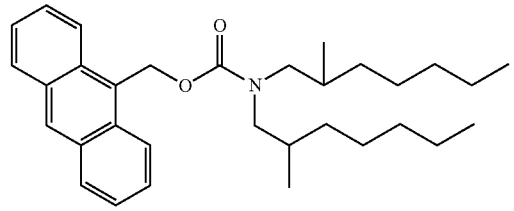
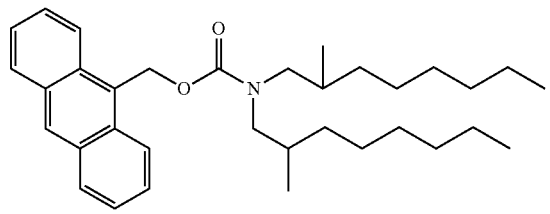
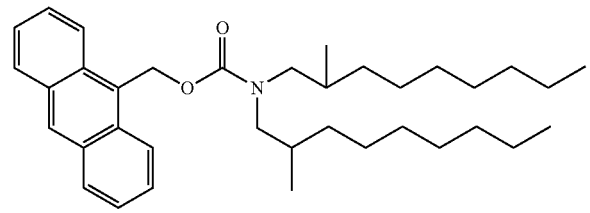
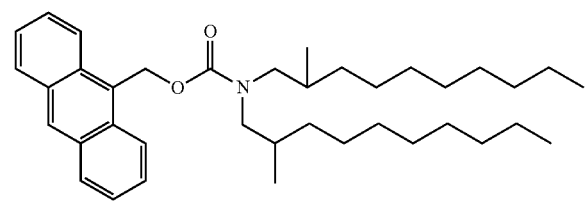
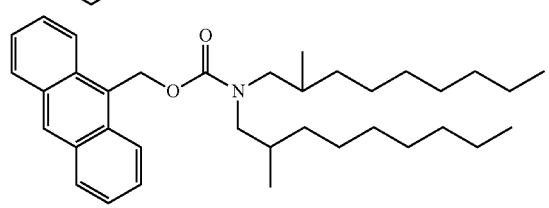
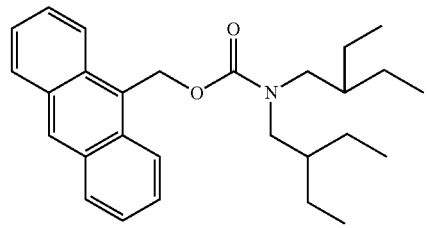
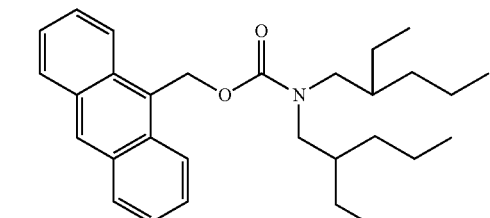
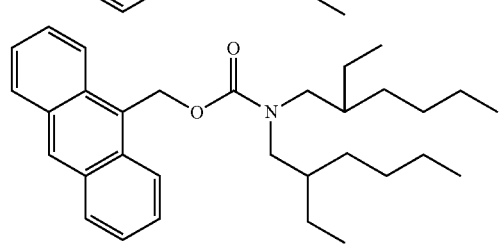

51
-continued
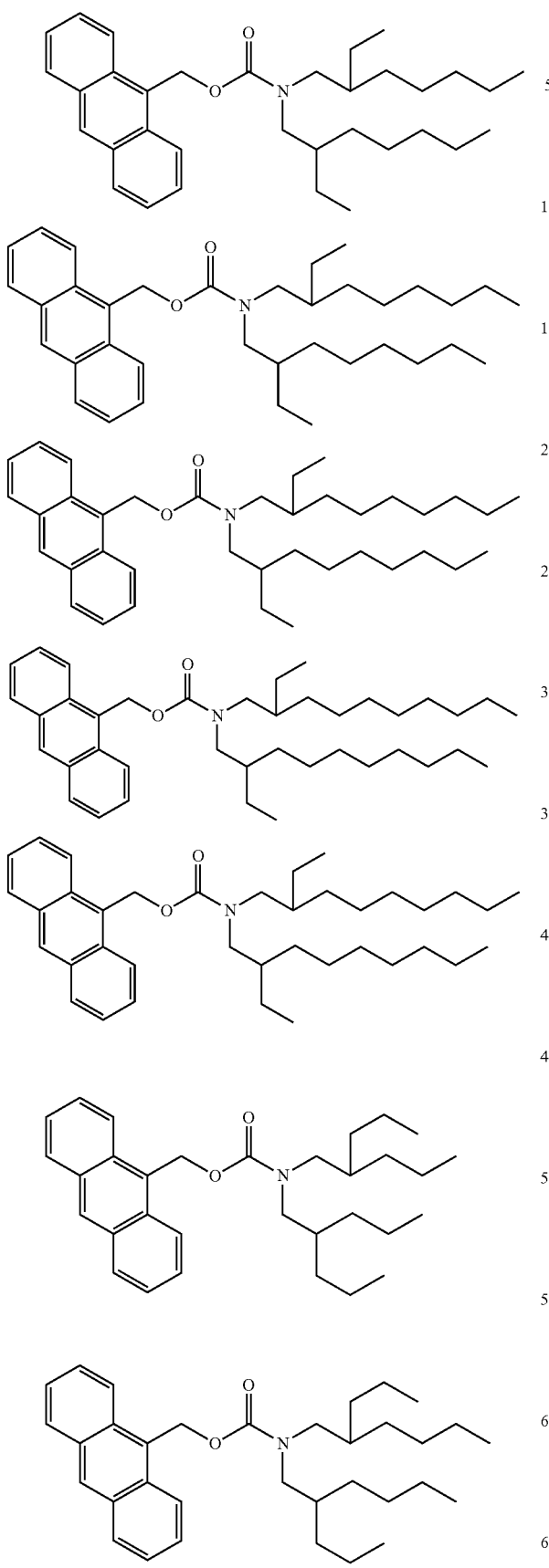
52
-continued
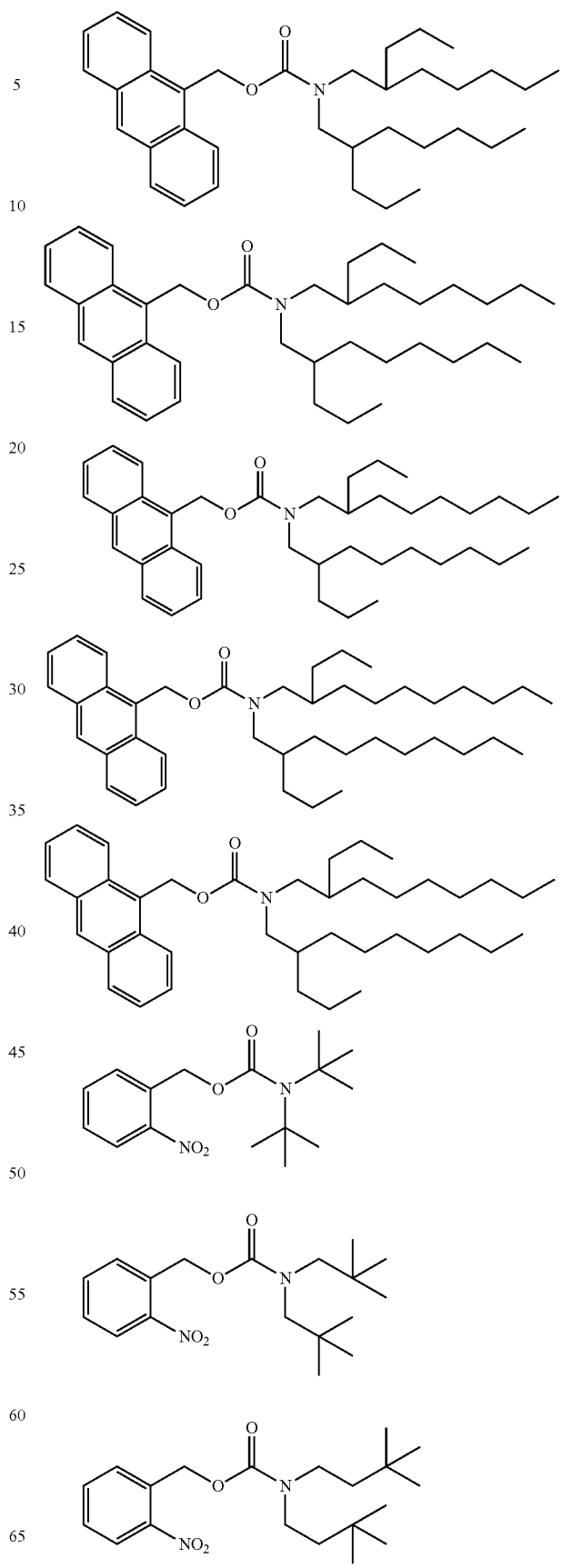

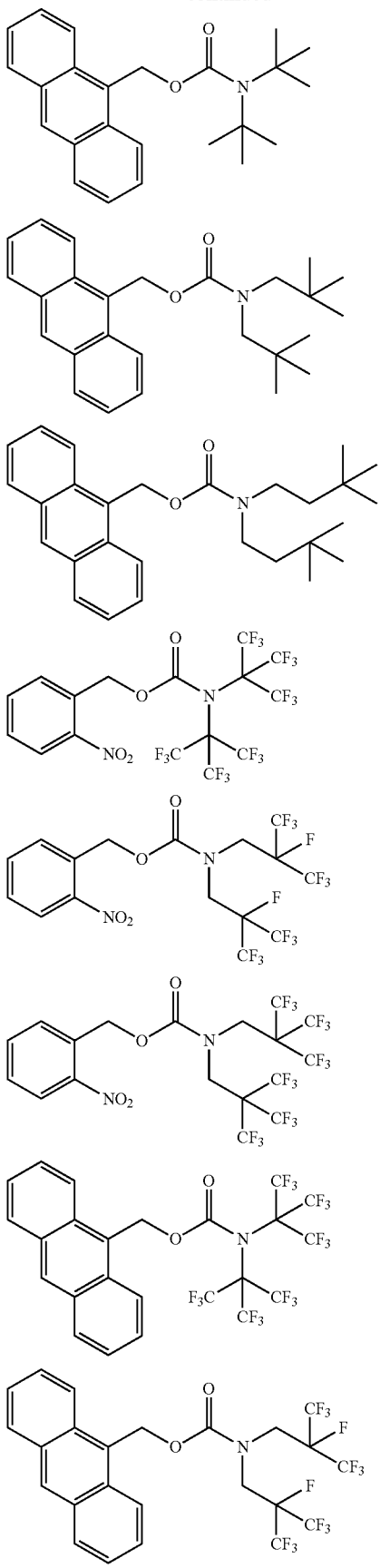

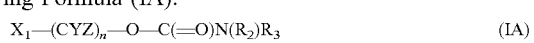

6. The method of claim 1 wherein the substrate is a semiconductor substrate.

7. A positive-acting photoresist composition comprising:
(1) a resin comprising photoacid-labile groups;
(2) one or more acid generators; and
(3) a photobase generator that corresponds to the following Formula (IA):

$$X_1-(CYZ)_n-O-C(=O)N(R_2)R_3 \quad \text{(IA)}$$

wherein $X_1$ is an optionally substituted aromatic group;
each Y and Z is independently hydrogen or a non-hydrogen substituent;
n is a positive integer; and
$R_2$ and $R_3$ are the same or different optionally substituted branched alkyl group having 4 or more carbon atoms.

8. The photoresist composition of claim 7 wherein $X_1$ is optionally substituted anthracenyl or phenyl.

9. The photoresist composition of claim 7 wherein $R_2$ and $R_3$ are each independently optionally substituted branched alkyl having 6 or more carbon atoms.

10. The photoresist composition of claim 7 wherein $R_2$ and/or $R_3$ are fluorinated branched alkyl having 4 or more carbon atoms.

11. The photoresist composition of claim 7 wherein the photobase generator is selected from among the following:

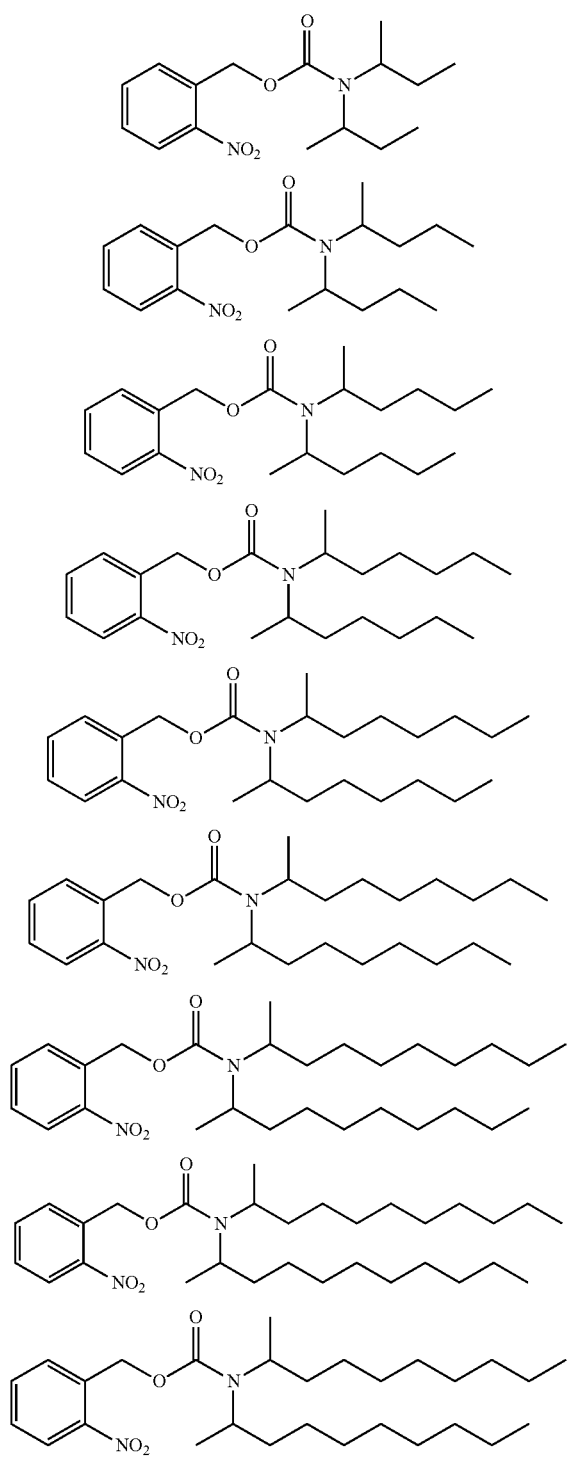
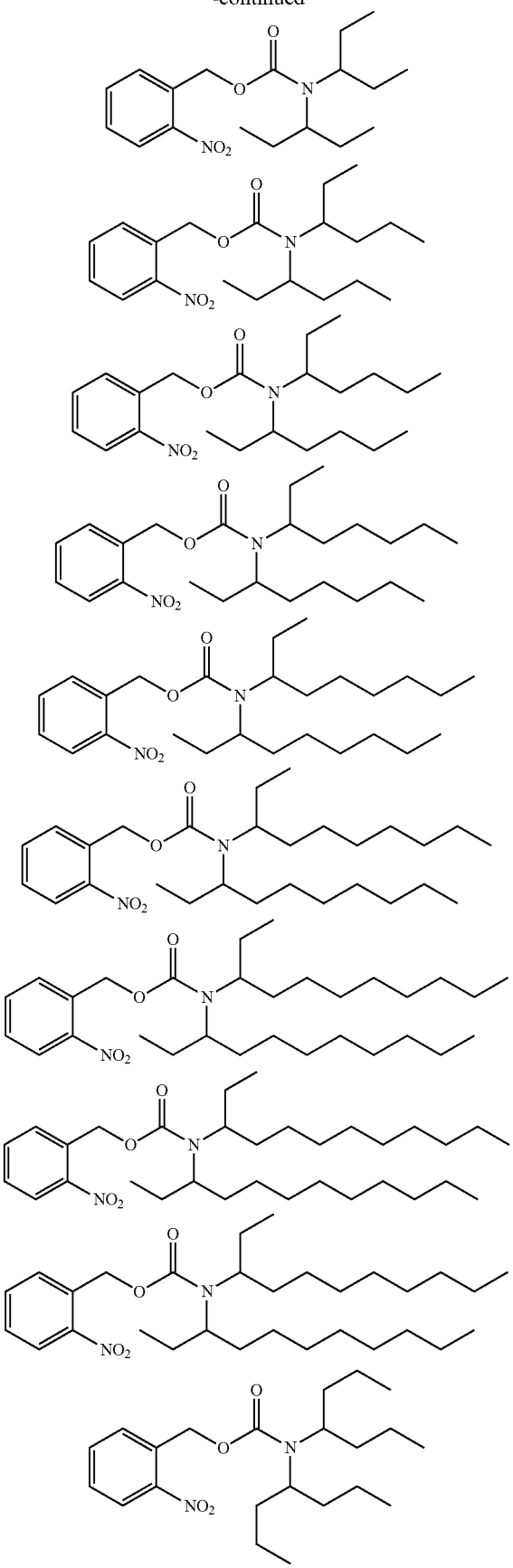

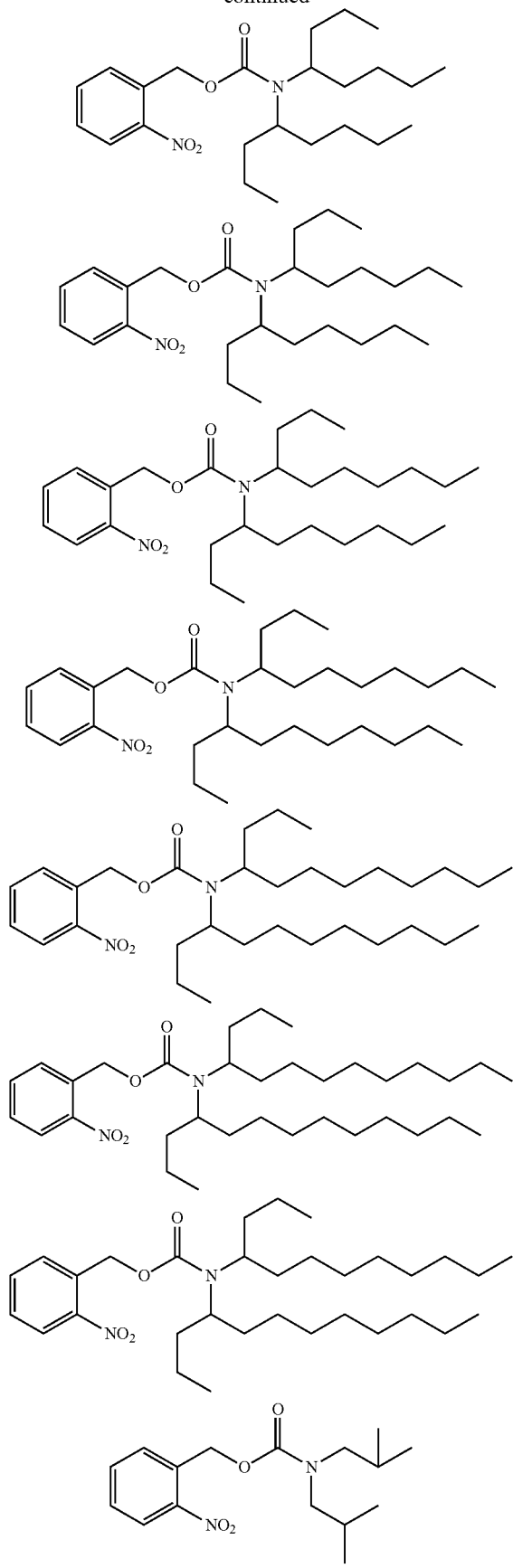
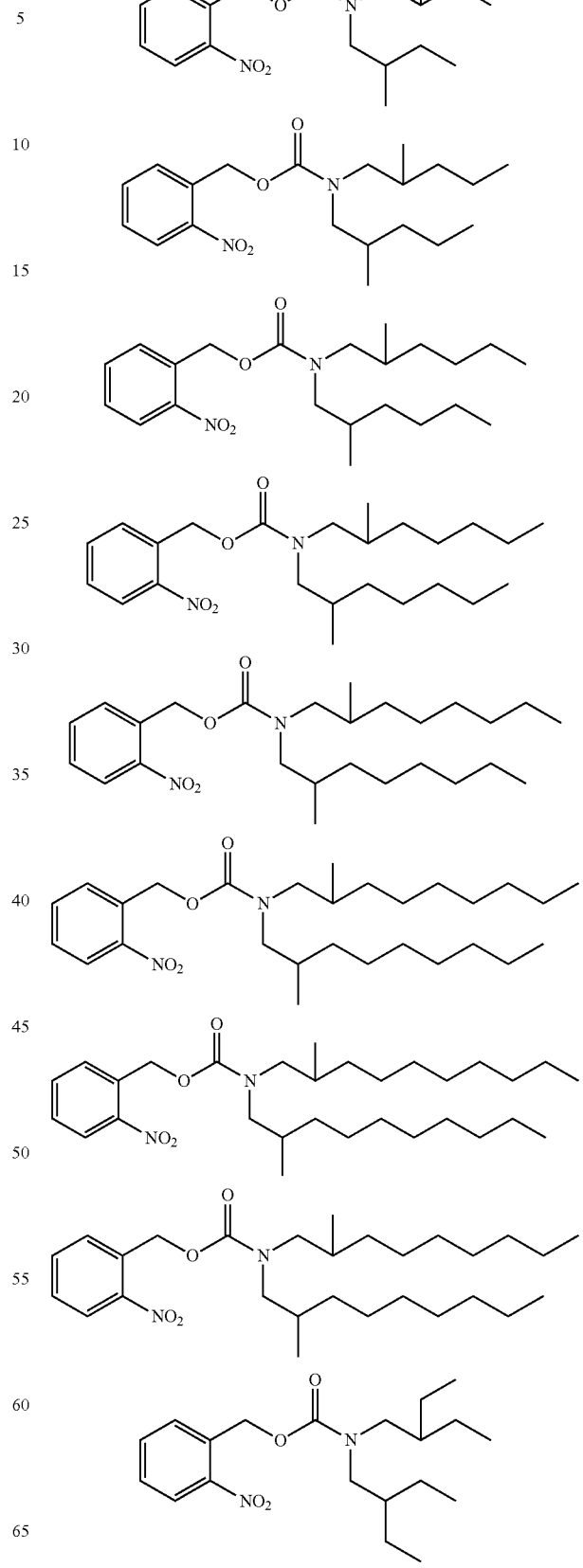

-continued

61
-continued
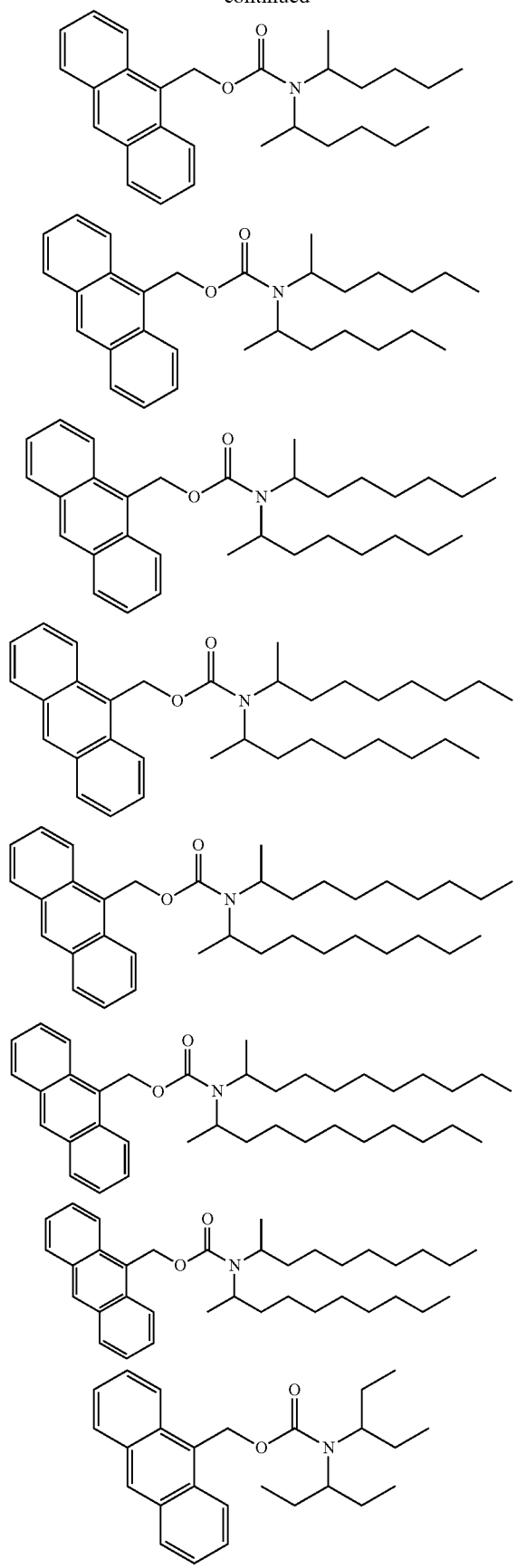
62
-continued
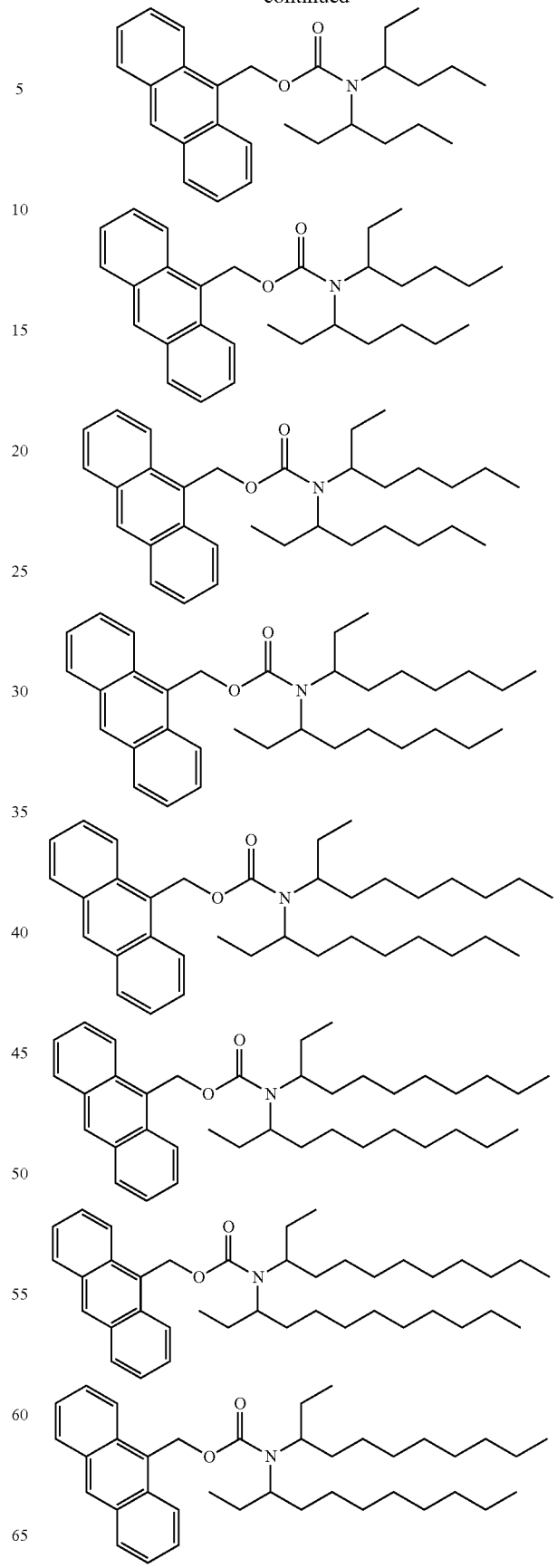

63
-continued
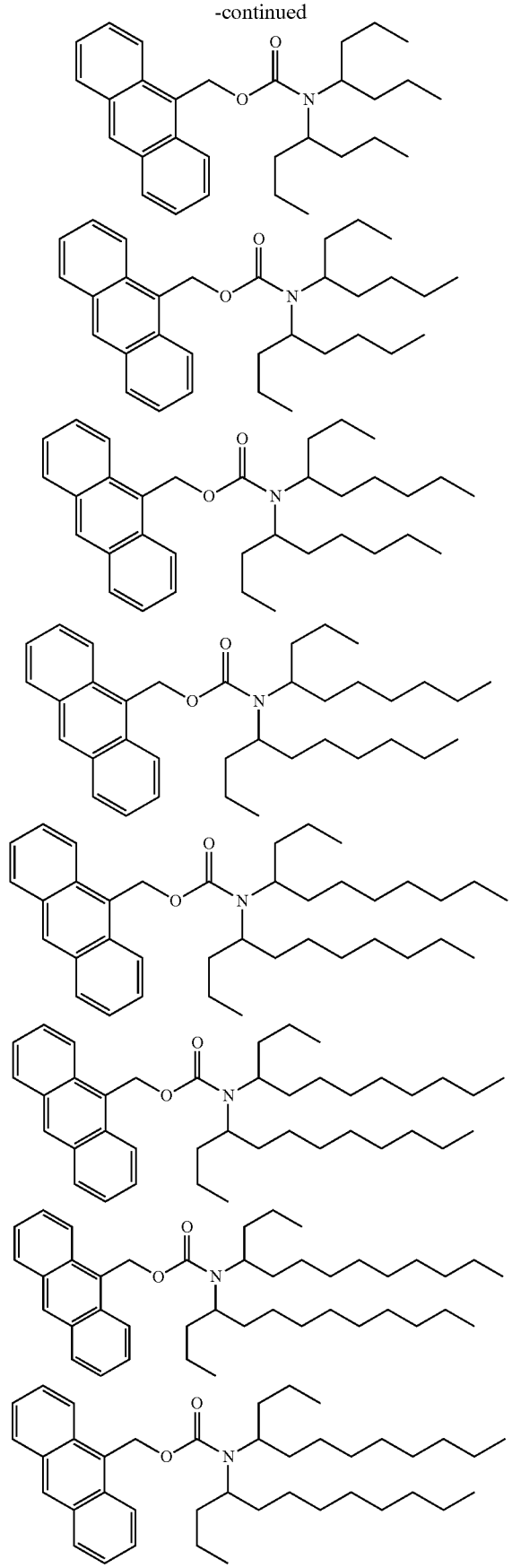
64
-continued
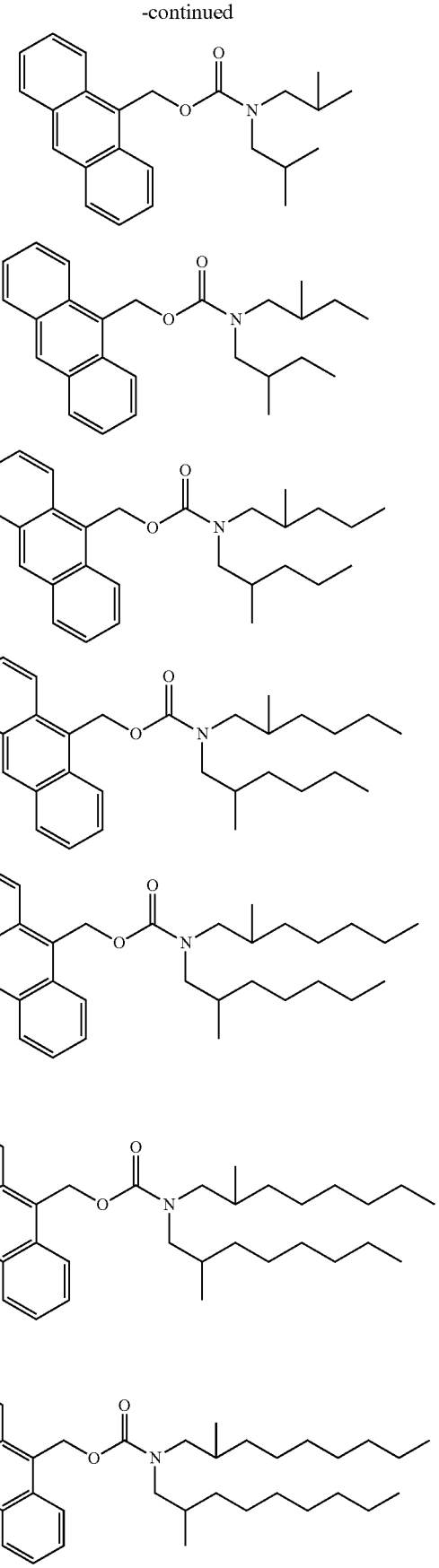

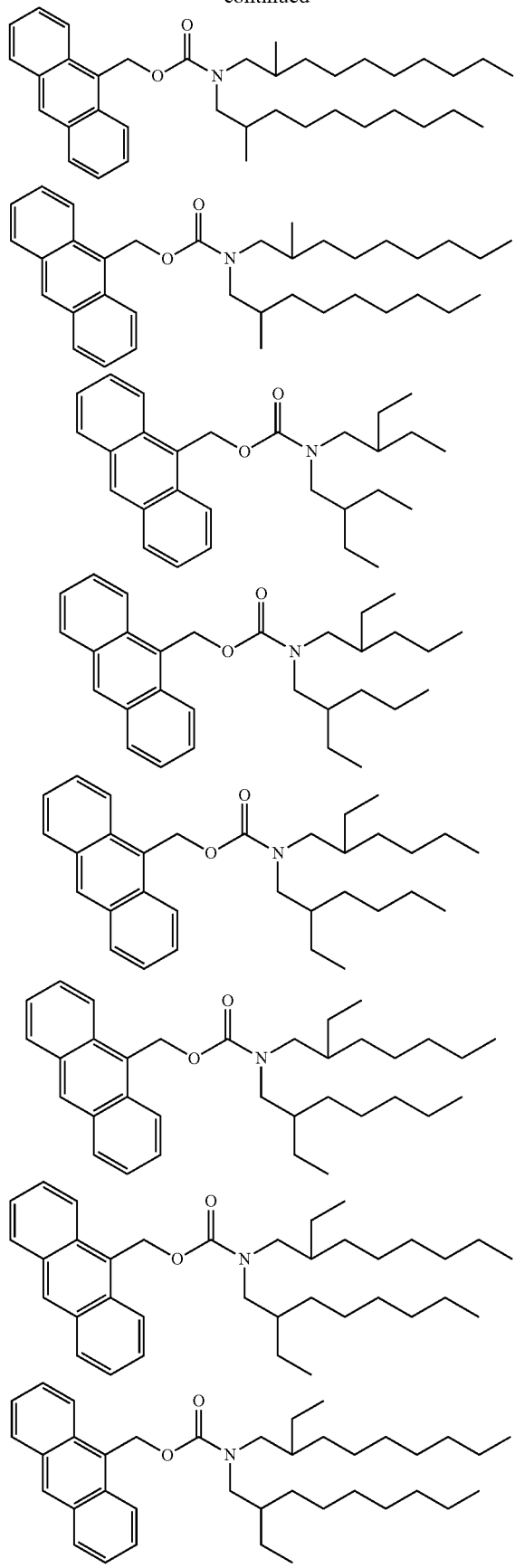
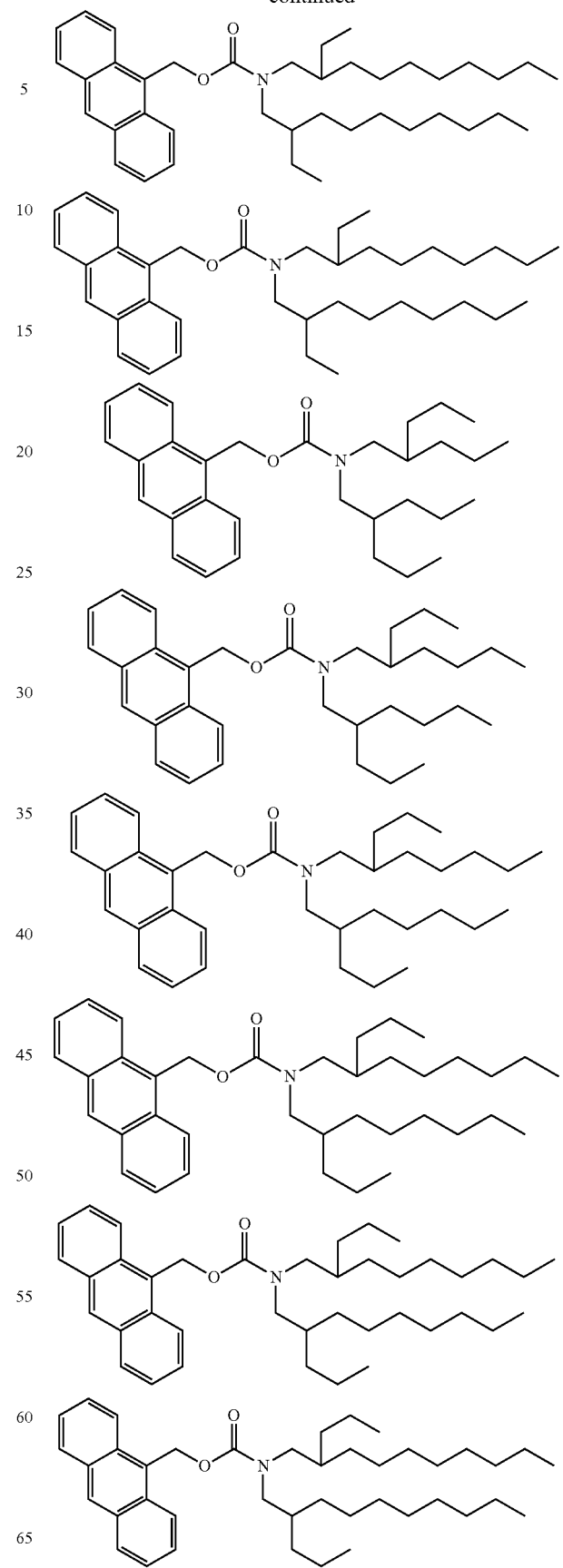

67
-continued
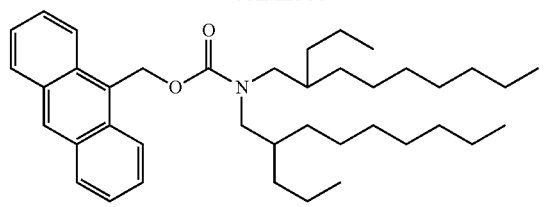
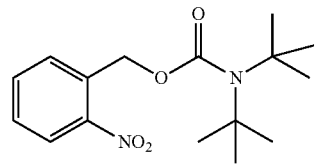
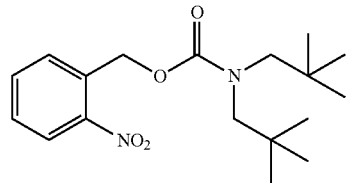
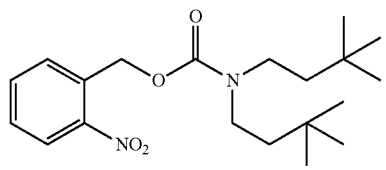
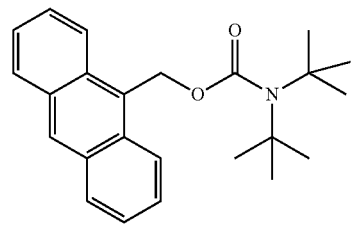
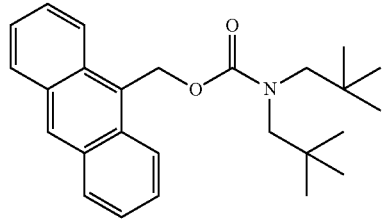
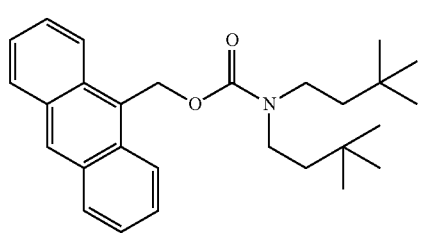
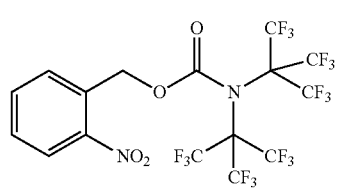
68
-continued
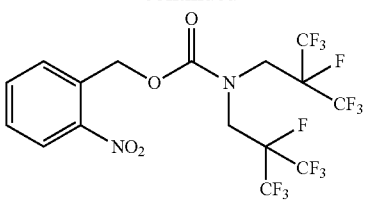
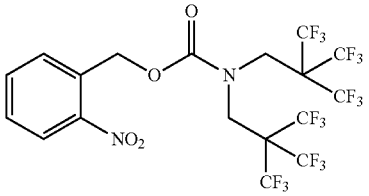
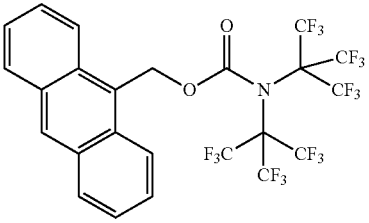
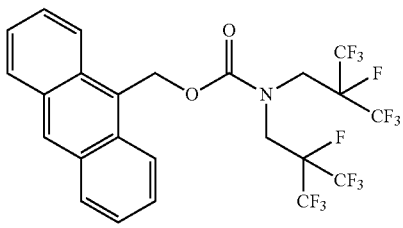
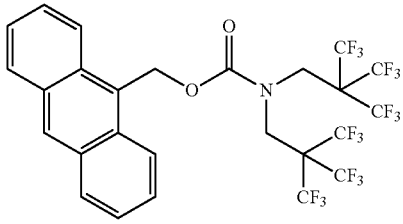
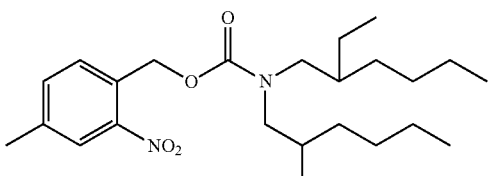
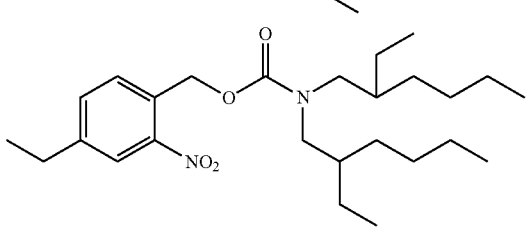
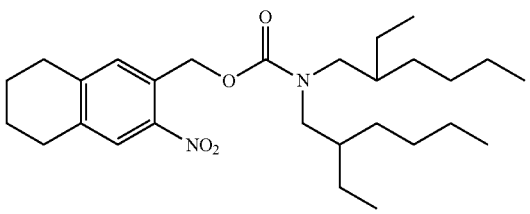

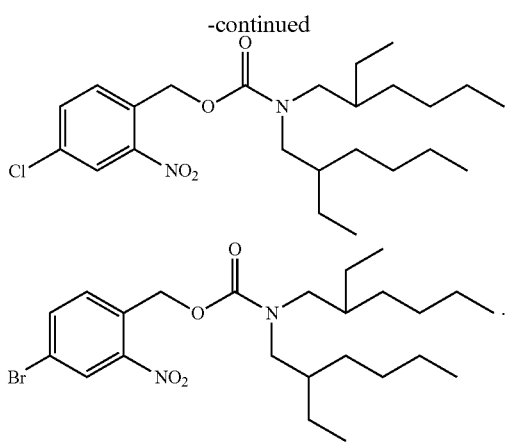

12. A positive-acting photoresist composition comprising:
(1) a resin;
(2) one or more acid generators; and
(3) a photobase generator that corresponds to the following Formula (IB):

$$X_1—(CY'{=}CZ')_n—(CY'Z')_{n'}—O—C({=}O)N(R_2)R_3 \quad (IB)$$

wherein $X_1$ is an optionally substituted aromatic group;
each Y' and Z' is independently hydrogen or a non-hydrogen substituent;
n and n' are each positive integer; and
$R_2$ and $R_3$ are the same or different optionally substituted linear, branched or cyclic aliphatic group or an optionally substituted aromatic group,
wherein at least one of $R_2$ and $R_3$ is an optionally substituted branched alkyl group having 4 or more carbon atoms.

13. A positive-acting photoresist composition comprising:
(1) a resin comprising photoacid-labile groups;
(2) one or more acid generators; and
(3) a photobase generator that corresponds to the following Formula (IA):

$$X_1—(CYZ)_n—O—C({=}O)N(R_2)R_3 \quad (IA)$$

wherein $X_1$ is an optionally substituted aromatic group, wherein the aromatic group is not substituted by a $NO_2$ group;
each Y and Z is independently hydrogen or a non-hydrogen substituent;
n is a positive integer; and
$R_2$ and $R_3$ are the same or different optionally substituted linear, branched or cyclic aliphatic group or an optionally substituted aromatic group,
wherein at least one of $R_2$ and $R_3$ is an optionally substituted branched alkyl group having 4 or more carbon atoms, and $R_2$ and $R_3$ are not substituted by a $CO_2H$ group or an ester group.

14. A method for forming a photolithographic pattern, comprising:
(a) applying a layer of a photoresist composition of claim 13 on a substrate;
(b) patternwise exposing the photoresist composition layer to activating radiation; and
(c) developing the exposed photoresist composition layer to provide a photoresist relief image.

* * * * *